(12) United States Patent
Borovsky et al.

(10) Patent No.: US 7,507,205 B2
(45) Date of Patent: Mar. 24, 2009

(54) STEERABLE ULTRASOUND CATHETER

(75) Inventors: Simcha Borovsky, Fair Lawn, NJ (US); Praveen Dala-Krishna, Bensalem, PA (US); Charles Bryan Byrd, Medford, NJ (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 1016 days.

(21) Appl. No.: 10/819,358

(22) Filed: Apr. 7, 2004

(65) Prior Publication Data

US 2005/0228290 A1 Oct. 13, 2005

(51) Int. Cl.
*A61B 8/14* (2006.01)

(52) U.S. Cl. .................... 600/466; 600/467; 600/471

(58) Field of Classification Search ................ 600/466, 600/437, 450, 137, 146
See application file for complete search history.

(56) References Cited

U.S. PATENT DOCUMENTS

| | | | |
|---|---|---|---|
| 4,161,121 A | 7/1979 | Zitelli et al. | |
| 4,241,610 A | 12/1980 | Anderson | |
| 4,462,408 A | 7/1984 | Silverstein et al. | |
| 4,519,260 A | 5/1985 | Fu et al. | |
| 4,576,177 A | 3/1986 | Webster, Jr. | |
| 4,605,009 A | 8/1986 | Pourcelot et al. | |
| 4,841,977 A | 6/1989 | Griffith et al. | |
| 4,890,268 A | 12/1989 | Smith et al. | |
| 4,917,097 A | 4/1990 | Proudian et al. | |
| 4,951,677 A * | 8/1990 | Crowley et al. | 600/463 |
| 5,002,059 A | 3/1991 | Crowley et al. | |
| 5,090,956 A | 2/1992 | McCoy | |
| 5,105,819 A | 4/1992 | Wollschlager et al. | |
| 5,152,294 A | 10/1992 | Mochizuki et al. | |
| 5,158,087 A | 10/1992 | Gatzke | |
| 5,170,793 A | 12/1992 | Takano et al. | |
| 5,195,968 A * | 3/1993 | Lundquist et al. | 604/95.04 |
| 5,254,088 A | 10/1993 | Lundquist et al. | |
| 5,279,559 A | 1/1994 | Barr | |
| 5,307,816 A | 5/1994 | Hashimoto et al. | |

(Continued)

OTHER PUBLICATIONS

Keith S. Dickerson et al., "Comparison of Conventional and Transverse Doppler Sonograms", J. Ultrasound Med., 1993, pp. 497-506, vol. 12.

(Continued)

*Primary Examiner*—Eric F Winakur
*Assistant Examiner*—Katherine L Fernandez
(74) *Attorney, Agent, or Firm*—Robert Hansen

(57) ABSTRACT

Steerable catheters are provided including an elongated flexible member having a proximal end, a distal end and a lumen extending therebetween (i.e., between the proximal end and the distal end). A plurality of electrical cables is bundled together and positioned within the lumen of the flexible member. The cross-section of the bundle of electrical cables is substantially ovular or rectangular so as to be bendable in two approximately opposite directions. Methods of steering such a catheter within a body include advancing the catheter within a body while a first force is applied to the bundle of electrical cables to cause the distal end of the elongate flexible member to form a bend. The catheter is farther advanced within the body while a second, opposite force is applied to the bundle of electrical cables to remove the bend in the distal end.

35 Claims, 20 Drawing Sheets

U.S. PATENT DOCUMENTS

| | | |
|---|---|---|
| 5,309,914 A | 5/1994 | Iinuma |
| 5,325,860 A | 7/1994 | Seward et al. |
| 5,336,182 A | 8/1994 | Lundquist et al. |
| 5,345,938 A | 9/1994 | Nishiki et al. |
| 5,345,940 A | 9/1994 | Seward et al. |
| 5,357,550 A | 10/1994 | Asahina et al. |
| 5,358,478 A | 10/1994 | Thompson et al. |
| 5,364,351 A | 11/1994 | Heinzelman et al. |
| 5,372,138 A | 12/1994 | Crowley et al. |
| 5,385,148 A | 1/1995 | Lesh et al. |
| 5,395,327 A | 3/1995 | Lundquist et al. |
| 5,438,997 A | 8/1995 | Sieben et al. |
| 5,456,258 A | 10/1995 | Kondo et al. |
| 5,456,664 A | 10/1995 | Heinzelman et al. |
| 5,470,350 A | 11/1995 | Buchholtz et al. |
| 5,499,630 A | 3/1996 | Hiki et al. |
| 5,515,853 A | 5/1996 | Smith et al. |
| 5,515,856 A | 5/1996 | Olstad et al. |
| 5,531,686 A | 7/1996 | Lundquist et al. |
| 5,560,362 A | 10/1996 | Sliwa, Jr. et al. |
| 5,588,432 A | 12/1996 | Crowley |
| 5,622,174 A | 4/1997 | Yamazaki |
| 5,662,116 A * | 9/1997 | Kondo et al. ................. 600/462 |
| 5,697,965 A | 12/1997 | Griffin, III |
| 5,699,805 A | 12/1997 | Seward et al. |
| 5,701,897 A | 12/1997 | Sano |
| 5,704,361 A | 1/1998 | Seward et al. |
| 5,713,363 A | 2/1998 | Seward et al. |
| 5,715,817 A | 2/1998 | Stevens-Wright et al. |
| 5,722,403 A | 3/1998 | McGee et al. |
| 5,749,364 A | 5/1998 | Sliwa, Jr. et al. |
| 5,788,636 A | 8/1998 | Curley |
| 5,795,299 A | 8/1998 | Eaton et al. |
| 5,797,848 A | 8/1998 | Marian et al. |
| 5,800,356 A | 9/1998 | Criton et al. |
| 5,807,324 A | 9/1998 | Griffin, III |
| 5,846,205 A | 12/1998 | Curley et al. |
| 5,888,577 A | 3/1999 | Griffin, III et al. |
| 5,891,088 A | 4/1999 | Thompson et al. |
| 5,906,579 A | 5/1999 | Vander Salm et al. |
| 5,916,168 A | 6/1999 | Pedersen et al. |
| 5,921,978 A | 7/1999 | Thompson et al. |
| 5,928,276 A | 7/1999 | Griffin, III et al. |
| 5,931,863 A | 8/1999 | Griffin, III et al. |
| 5,935,102 A | 8/1999 | Bowden et al. |
| 5,938,616 A | 8/1999 | Eaton et al. |
| 5,954,654 A | 9/1999 | Eaton et al. |
| 6,013,072 A | 1/2000 | Winston et al. |
| 6,033,378 A | 3/2000 | Lundquist et al. |
| 6,039,693 A | 3/2000 | Seward et al. |
| 6,085,117 A | 7/2000 | Griffin, III et al. |
| 6,144,870 A | 11/2000 | Griffin, III |
| 6,171,248 B1 | 1/2001 | Hossack et al. |
| 6,173,205 B1 * | 1/2001 | Griffin et al. ................. 607/122 |
| 6,190,353 B1 | 2/2001 | Makower et al. |
| 6,210,333 B1 | 4/2001 | Gardner et al. |
| 6,224,556 B1 | 5/2001 | Schwartz et al. |
| 6,228,028 B1 | 5/2001 | Klein et al. |
| 6,228,032 B1 | 5/2001 | Eaton et al. |
| 6,261,246 B1 | 7/2001 | Pantages et al. |
| 6,293,943 B1 | 9/2001 | Pansecu et al. |
| 6,306,096 B1 | 10/2001 | Seward et al. |
| 6,306,097 B1 * | 10/2001 | Park et al. ................... 600/466 |
| 6,310,828 B1 | 10/2001 | Mumm et al. |
| 6,360,027 B1 | 3/2002 | Hossack et al. |
| 6,368,275 B1 | 4/2002 | Sliwa et al. |
| 6,385,489 B1 | 5/2002 | Griffin, III et al. |
| 6,398,731 B1 | 6/2002 | Mumm et al. |
| 6,423,002 B1 | 7/2002 | Hossack |
| 6,440,488 B2 | 8/2002 | Griffin, III et al. |
| 6,443,894 B1 | 9/2002 | Sumanaweera et al. |
| 6,475,148 B1 | 11/2002 | Jackson et al. |
| 6,475,149 B1 | 11/2002 | Sumanaweera |
| 6,482,161 B1 | 11/2002 | Sumanaweera et al. |
| 6,485,455 B1 | 11/2002 | Thompson et al. |
| 6,491,633 B1 | 12/2002 | Krishnan et al. |
| 6,503,202 B1 | 1/2003 | Hossack et al. |
| 6,517,488 B1 | 2/2003 | Hossack |
| 6,527,717 B1 | 3/2003 | Jackson et al. |
| 6,532,378 B2 | 3/2003 | Saksena et al. |
| 6,554,770 B1 | 4/2003 | Sumanaweera et al. |
| 6,589,182 B1 | 7/2003 | Loftman et al. |
| 6,605,043 B1 | 8/2003 | Dreschel et al. |
| 6,607,488 B1 | 8/2003 | Jackson et al. |
| 6,607,528 B1 | 8/2003 | Quick et al. |
| 6,612,992 B1 | 9/2003 | Hossack et al. |
| 6,645,147 B1 | 11/2003 | Jackson et al. |
| 6,648,875 B2 | 11/2003 | Simpson et al. |
| 6,709,396 B2 | 3/2004 | Flesch et al. |
| 6,908,434 B1 | 6/2005 | Jenkins et al. |
| 6,923,768 B2 | 8/2005 | Camus et al. |
| 7,029,467 B2 * | 4/2006 | Currier et al. ................ 604/525 |
| 2003/0045796 A1 | 3/2003 | Friedman |
| 2003/0158483 A1 | 8/2003 | Jackson et al. |
| 2004/0097805 A1 | 5/2004 | Verard et al. |
| 2004/0249282 A1 | 12/2004 | Olslad |
| 2004/0254442 A1 * | 12/2004 | Williams et al. ............. 600/407 |
| 2005/0203390 A1 | 9/2005 | Torp et al. |

OTHER PUBLICATIONS

David J. Sahn, "Phased Arrays for Multiplane Esophageal Echos in Infants", Summary Statement, Diagnostic Radiology Study Section, Jun. 1990.

David J. Sahn, "Instrumentation and Physical Factors Related to Visualization of Stenotic and Regurgitant Jets by Doppler Color Flow Mapping", JACC, Nov. 1988, pp. 1354-1365, vol. 12, No. 5.

David J. Sahn, "Advances in Ultrasound Imaging for Congenital Heart Disease Diagnosis and Management", Pediatric Cardiology, Nov. 26-Dec. 1, 1989, Proceedings of the III World Congress of Pediatric Cardiology, Bangkok.

David J. Sahn et al., "Important Rolesof Transeophageal Color Doppler Flow Mapping Studies (TEE) in Infants with Congenital Heart Disease", Supplement to Journal of the American College of Cardiology, Feb. 1990, vol. 15, No. 2 (Supplement A).

David J. Sahn, "Applications of Color Flow Mapping in Pediatric Cardiology", Cardiology Clinics, May 1989, pp. 255-264, vol. 7, No. 2.

David J. Sahn et al., "Miniaturized High Frequency Phased Array Devices for High Resolution Neonatal and Intraoperative Imaging", Supplement to Journal of the American College of Cardiology, Feb. 1990, vol. 15, No. 2 (Supplement A).

Piero Tortoli et al., "Velocity Magnitude Estimation with Linear Arrays Using Doppler Bandwidth", Ultrasounics, 2001, pp. 157-161, vol. 39.

Lilliam M. Valdes-Cruz et al., "Transvascular Intracardiac Applications of a Miniaturized Phase-Array Ultrasonic Endoscope", Brief Rapid Communication, Mar. 1991, pp. 1023-1027, vol. 83, No. 3.

Lilliam M. Valdes-Cruz et al., "Experimental Animal Investigations of the Potential for New Approaches to Diagnostic Cardiac Imaging in Infants and Small Premature Infants from Intracardiac and Trasesophageal Approaches Using a 20MHz Real Time Ultrasound Imaging Catheter", Supplement to Journal of the American College of Cardiology, Feb. 1989, vol. 13, No. 2 (Supplement A).

P.N.T. Wells, "Velocity, Absorption and Attenuation in Biological Materials", Biomedical Ultrasonics, 1977, pp. 110-144.

Antonio L. Bartorelli, M.D. et al., "Plaque Characterization of Atherosclerotic Coronary Arteries by Intravascular Ultrasound", Echocardiography: A Journal of CV Ultrasound & Allied Tech, 1990, pp. 389-395, vol. 7, No. 4.

N. Bom et al., "Early and recent intraluminal ultrasound devices", International Journal of Cardiac Imaging, 1989, pp. 79-88, vol. 4.

R.J. Crowley et al., "Optimized ultrasound imaging catheters for use in the vascular system", International Journal of Cardiac Imaging, 1989, pp. 145-151, vol. 4.

R.J. Crowley, et al., "Ultrasound guided therapeutic catheters: recent developments and clinical results", International Journal of Cardiac Imaging, 1991, pp. 145-156, vol. 6.

Richard A. Carleton, M.D., et al., "Measurement of Left Ventricular Diameter In the Dog by Cardiac Catheterization", Circulation Research, May 1968, pp. 545-558, vol. XXII.

Taher Elkadi et al., "Importance of Color Flow Doppler (CFD) Imaging of the Right Ventricular Outflow Tract and Pulmonary Arteries by Transesophageal Echocardiography (TEE) During Surgery for CHD", Supplement III Circulation, Oct. 1990, p. III-438, vol. 82, No. 4.

Philip C. Currie, "Transeosphageal Echocardiography New Window to the Hearth", Circulation, Jul. 1989, pp. 215-217, vol. 88, No. 1.

Steven Schwartz et al., "In Vivo Intracardiac 2-D Echocardiography: Effects of Transducer Frequency, Imaging Approached and Comparison with Fiberoptic Angioscopy", JACC, Feb. 1990, pp, 29A, vol. 15, No. 2.

J. Souquet et al., "Transesophageal Phased Array for Imaging the Heart", IEEE Transactions on Biomedical Engineering, Oct. 1982, pp. 707-712, vol. BME-29, No. 10.

Craig J. Hartley, "Review of Intracoronary Doppler catheters", International Journal of Cardiac Imaging, 1989, pp. 159-168, vol. 4.

John McB. Hodgson et al., "Percutaneous Intravascular Ultrasound Imaging: Validaton of a Real-Time Synthetic Aperture Array Catheter", American Journal of Cardiac Imaging, Mar. 1991, pp. 56-71, vol. 5, No. 1.

J. McB. Hodgson et al., "Clinical percutaneous imaging of coronary anatomy using an over-the-wire ultrasound catheter system", International Journal of Cardiact Imaging, 1989, pp. 187-193, vol. 4.

Brenda S. Kusay et al., "Realtime in Vivo Intracardiac Two-Dimensional Echocardiography and Color Flow Imaging: Approaches, Imaging Planes, and Echo Anatomy", Abstracts of the 62$^{nd}$ Scientific Sessions, 1989, p. II-581.

Charles T. Lancee, "A Transesophageal Phased Array Transducer for Ultrasonic Imaging of the Heart", 1987.

Natesa Pandian et al., "Enhanced Depth of Field in Intracardiac 2-D Echocardiography with a New Prototype, Low Frequency (12 MHz, 9 French) Ultrasound Catheter", Supplemental III Circulation, Oct. 1990, p. III-442, vol. 82, No. 4.

Natesa G. Pandian, M.D. et al., "Intravascular and Intracardiac Ultrasound Imaging: Current Research and Future Directions", Echocardiography: A Journal of CV Ultrasound & Allied Tech., 1990, pp. 377-387, vol. 7, No. 4.

Natesa G. Pandian, M.D. et al., "Intracardiac, Intravascular, Two-Dimensional, High-Frequency Ultrasound Imaging of Pulmonary Artery and Its Branches in Humans and Animals", Circulation, Jun. 1990, pp. 2007-2012, vol. 81, No. 6.

F. Ricou et al., "Applications of intravascular scanning and transesophageal echocardiography in congenital heart disease: tradeoffs and the merging of technologies", International Journal of Cardiac Imaging, 1991, pp. 221-230, vol. 6.

Samuel B. Ritter, M.D., et al., "Transesophageal real time Doppler flow imaging in congenital heart disease: experience with a new pediatric trasducer probe", 1989, Dynamedia, Inc.

Samuel B. Ritter, M.D., et al., "Pediatric Transesophageal Color Flow Imaging: Smaller Probes for Smaller Hearts", 1989.

David J. Sahn, M.D., et al., "Important Roles of Transesophageal Color Doppler Flow Mapping Studies (TEE) in Infants With Congenital Heart Disease", IACC, Feb. 1990, p. 204A, vol. 15, No. 2.

David J. Sahn, M.D. et al., "Miniaturized High Frequency Phased Array Devices for High Resolution Neonatal and Intraoperative Imaging", JACC, Feb. 1990, p. 10A, vol. 15, No. 2.

David J. Sahn, M.D., et al., "Phased Arrays for Multiplane Esophageal Echos in Infants", Grant Application, Department of Health and Human Services Public Health Service, 1992.

Steven Schwartz, M.D., et al., "Intracardiac Echocardioraphic Guidance and Monitoring During Aortic and Mitral Balloon Valvuloplasty", JACC, Feb. 1990, p. 104A, vol. 15, No. 2.

James B. Seward, M.D. et al., "Biplanar Transesophageal Echocardiography: Anatomic Correlations, Image Orientation, and Clinical Applications", Mayo Clin Proc., 1990, pp. 1198-1213, vol. 65.

James B. Seward, M.D. et al., "Wide-Field Transesophageal Echocardiographic Tomography: Feasibility Study", Mayo Clin Proc. 1990, pp. 31-37, vol. 65.

Khalid H. Sheikh, M.D., et al., "Interventional Applications of Intravascular Ultrasound Imaging: Initial Experience and Future Perspectives", Echocadiography: A Journal of CV Ultrasound & Allied Tech., pp. 433-441, vol. 7, No. 4.

Paul G. Yock, M.D., et al., "Two-Dimensional Intravascular Ultrasound: Technical Development and Initial Clinical Experience", Journal of American Society of Echocardiography, 1989, pp. 296-304, vol. 2, No. 4.

Paul G. Yock, M.D. et al., "Real-Time, Two-Dimensional Catheter Ultrasound: A New Technique for High-Resolution Intravascular Imaging", JACC, Feb. 1988, p. 130A, vol. 11, No. 2.

P. Yock et al., "Intravascular Two-Dimensional Catheter Ultrasound: Initial Clinical Studies", Abstracts of the 61$^{st}$ Scientist Sessions, p. II-21.

Michael J. Eberle et al., "Validation of a New Real Time Percotaneous Intravascular Ultrasound Imaging Catheter", Abstracts of the 61$^{st}$ Scientist Sessions, p. II-21.

Natasa Pandian et al., "Intralurolonal Ultrasound Angloscopic Detection of Arterial Dissection and Intimal Flaps: In Vitro and In Vivo Studies", Abstracts of the 61$^{st}$ Scientist Sessions, p. II-21.

John A. Mallery et al., "Evaluation of an Intravascular ultrasound Imaging Catheter in Porcine Peripheral and Coronary Arteries In Vivo", Abstracts of the 61$^{st}$ Scientist Sessions, p. II-21.

Andrew Wintraub, M.D., "Realtime Intracardiac Two-Dimensional Echocardiography in the Catheterization Laboratory in Humans", Intravascular Imaging I, Mar. 19, 1990.

International Search Reprot (ISR) for PCT/US05/011545, Dec. 5, 2006.

Written Opinion of International Search Authority for PCT/US05/011545, Dec. 6, 2006.

International Preliminary Report on Patentability for PCT/US05/011545, Dec. 6, 2006.

* cited by examiner

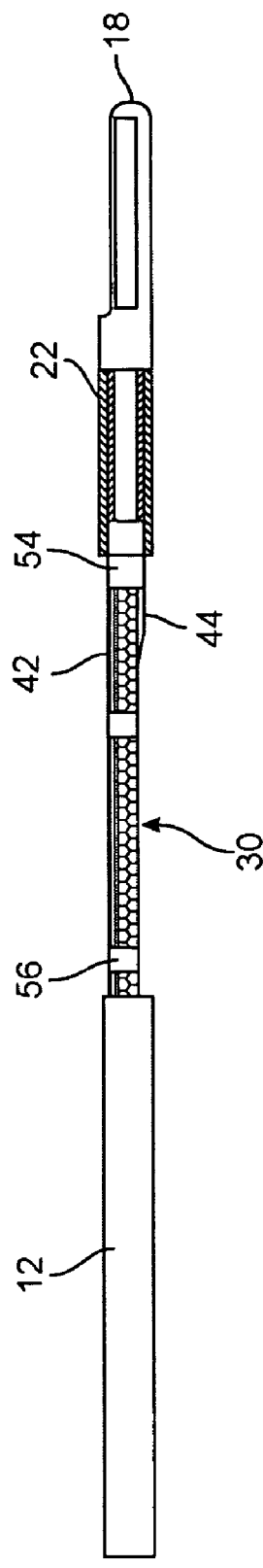
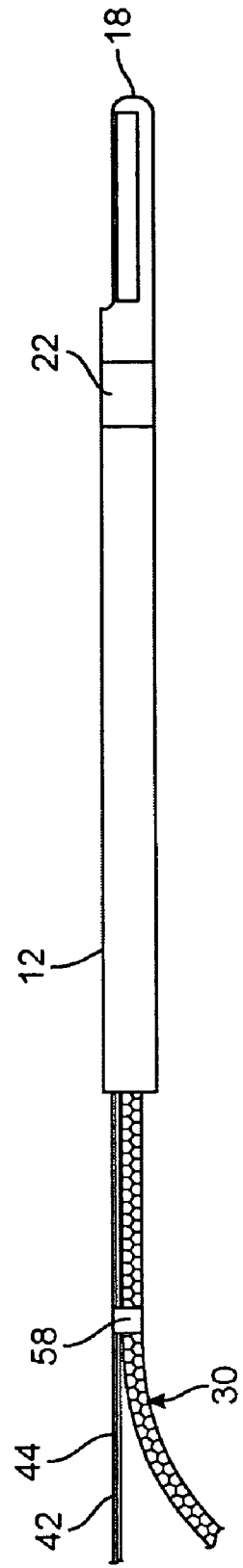

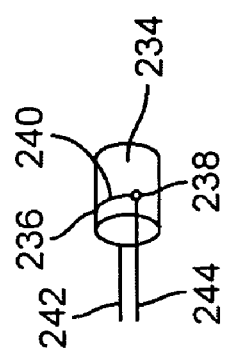
FIG. 15C
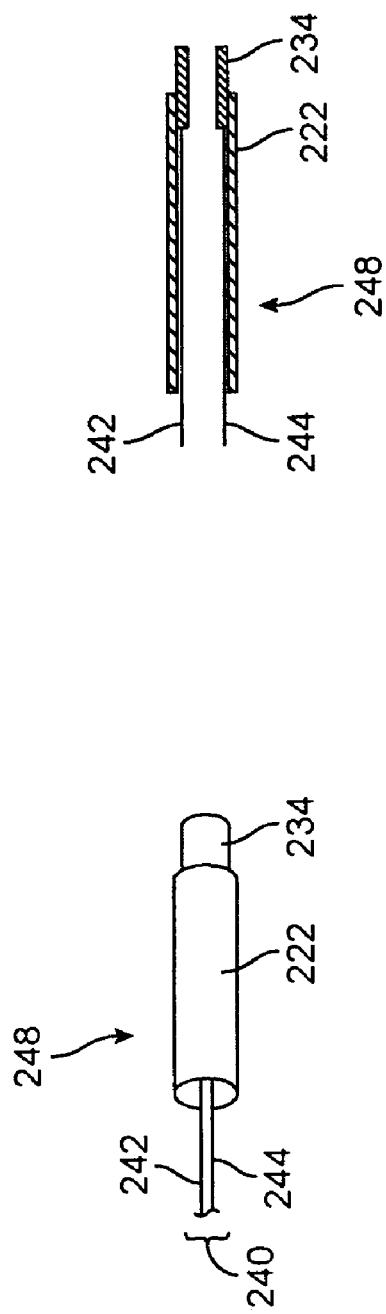
FIG. 15D
FIG. 15
FIG. 15B
FIG. 15A

STEERABLE ULTRASOUND CATHETER

This application claims priority to U.S. patent application Ser. No. 10/819,358, filed Apr. 7, 2004, the disclosure of which is incorporated herein in its entirety.

BACKGROUND OF THE INVENTION

1. Field of the Invention

The present invention relates generally to steerable catheters, and more particularly to steerable ultrasound imaging catheters that can be maneuvered intravascularly throughout the cardiovascular system.

2. Description of the Related Art

Catheters for insertion and deployment within blood vessels and cardiac chambers are well-known in the art.

Endocardial catheter recording, mapping, and imaging probes have clinical roles in diagnosis and treatment of cardiovascular ailments including direct ablation, surgical, and drug therapies, in the treatment of supra-ventricular tachycardia, ventricular tachycardia, atrial flutter, atrial fibrillation and other arrhythmias. The addition of ultrasound imaging catheters to the ensemble of electrophysiology catheters has greatly improved the physician's ability to visualize endocardial structures, thus improving diagnosis and targeted ablation.

The success and advancement of current therapies will benefit from the development and use of more precise catheter positioning and localization techniques within a patient's body that will allow accurate anatomical determination of abnormal conductive pathways and other arrhythmogenic sites.

Improvements are needed in catheter steering systems in order to permit ultrasound imaging probes to reach specific targets and view regions of interests, such as within a patient's heart. Also, improved flexibility will permit the attending physician to more accurately maneuver and direct the ultrasound imaging catheter tip. Placement of prior art catheters within the heart has been generally restricted to areas which can be repeatedly accessed by the electrophysiologist. These areas include the (high right atrium) HRA, the (right ventricular apex) RVA, the (right ventricular outflow tract) RVOT, the coronary sinus, the atrial ventricular node (AV node) and near the HIS bundle. To obtain meaningful information about additional placement sites, the number of electrograms recorded over a given area may be increased, and the precise position of the electrode array of the distal tip portion of the catheter may be varied. Some of these additional sites include atrial sites above the tricuspid and mitral valves, ventricular sites circumferential to the mitral and tricuspid valve leaflets, distal areas of the coronary sinus and great cardiac vein, the AV nodal area and the left ventricle, in addition to other sites as would be readily apparent to one of ordinary skill in the art after reading this disclosure.

One area of advancement in improving catheter positioning techniques and accessing additional recording sites within a patient's heart is the use of steerable catheters. One type of prior art steerable catheter permits maneuvering the catheter to specific, otherwise inaccessible sites by being shaped specifically to access the particular site. Although perhaps useful for some less inaccessible sites, the use of this type of catheter is limited, not very practical, and not helpful in reaching sites requiring active articulation during placement.

Other prior art steerable catheters attempt to improve placement maneuverability by having bendable tips. These catheters include a relatively soft and flexible distal tip portion of a certain length attached to a proximal shaft made from a relatively stiffer material. Generally, the tip may be selectively deflected but only in a prescribed arc defining a plane. The tip of the catheter bends in one planar direction, with the bend having a fixed, predetermined radius of curvature, typically around four inches. A steering cable attached to the distal tip portion at or near the tip and running down the interior of the catheter is pulled proximally while the catheter shaft is restrained, thus causing the tip to deflect. Alternatively, the steering cable is restrained while the shaft portion is advanced distally, producing the same effect.

A disadvantage of the above-described preformed and deflecting tip type catheters is that the tip of the catheter in each case may be deflected or steered only in a prescribed configuration in only a single plane which cannot be altered during or after its placement. That is, the steerable tip has a single radius of curvature which is fixed, thus restricting the accessibility of the distal tip to certain anatomical sites, while other sites may not be accessible at all. Further, in order to direct the catheter tip into a passage at an angle to the deflection plane, the catheter must be straightened, rotated to align with the passage and then deflected. In some passages this may not be possible. Also, in the case of ultrasound imaging catheters, rotating the catheter may direct the imaging plane away from areas of interest.

As a result of the above described disadvantages of prior art steerable catheters, the electrophysiologist must obtain and maintain not one but a set of similar steerable electrode catheters for use during any single clinical evaluation of a patient. For example, the user will have on hand a catheter having a steerable tip having a small radius of curvature; another with a medium radius of curvature and a third with a relatively large radius of curvature. While this availability of differently radiused tips is beneficial, it is often not known by the electrophysiologist which size will be required prior to a diagnostic or therapeutic intracardiac procedure. Moreover, similar tip placements may require different radiused tips from one individual to another, even those of the same general body size and mass. When it is discovered by the electrophysiologist that a catheter then placed in a patient has an incorrectly radiused tip for the required procedure, the catheter must be completely withdrawn from the patient (through whichever one of the femoral, subclavian, jugular or brachial approaches was used), and a new properly radiused electrode catheter tip must be reintroduced into the heart. This substitution may take up to two hours or more to complete, including the time required to precisely reposition the electrode tip.

Moreover, the initially selected, but improperly sized catheter must generally be discarded, never having been actually used for its intended purpose, as such devices are intended as "single use only" devices for a variety of safety reasons. Steerable catheters are relatively expensive devices, and this waste of an otherwise good device is especially troublesome.

In response to these problems, steerable catheters have been developed which have an adjustable radius of curvature. These catheters require a radius control mechanism in addition to the steering control mechanism, which imposes additional level of complexity to their manufacture and use.

Other disadvantages are related to the limitations inherent in current pull cable steering systems. Such steering systems typically include a flat stainless steel shim or similar spring-like element in the area where the catheter tip is to be bent. One or more pull cables are secured to the shim or portion of the catheter adjacent the distal end of the shim and extend the length of the catheter to be manipulated by the physician in order to steer the catheter. These steering systems require additional locking for the bend or curve to be fixed for any period of time. Deflectable catheter tips of the type just described are generally resiliently biased due to the springs, which cause the catheter tips to return to a straight configuration when not acted upon by the pull cable mechanisms for causing tip deflection. Another drawback with such catheters, as a result of this resiliency, is the undesired tendency of the tip to return to an undeflected position, or to merely change the amount of deflection, during the course of the electrophysiological procedure. Locking mechanisms have been employed to secure the deflection, but this requires an additional step for the physician using the catheter. Such excessive maneuvering and the additional step of locking the catheter exteriorly of the patient is difficult, frustrating, time consuming and inefficient to the physician performing a delicate procedure, and is thus inherently more risky for the patient undergoing that procedure.

Another disadvantage to the current pull cable systems becomes even more evident when applied to ultrasound catheters, particularly those that are also used for electrophysiology applications. Most ultrasound catheters have a large number of ultrasound elements that form the transducer, and each requires a separate coaxial cable running through the length of the catheter body. This is in addition to the insulated electrical signal wires that run through the catheter bodies. All of these wires and cables leave little room for a spring shim or the like.

Another disadvantage in current imaging catheters is the cross-sectional diameter required to accommodate the steering cables and electrical wiring for imaging components. For example, a transducer with just sixty-four elements requires at least sixty-four cables running through the catheter, in addition to the steering cables. The number of cables increases with the number of transducer elements. For that reason, imaging catheters typically are no smaller than 10 French in diameter. Catheters with diameters of less than 10 French could be useful to navigate through small vessels in the body and to reduce potential injury to patients.

Therefore, a need exists for a steerable ultrasound catheter that is easier to construct, has a flexible and versatile distal end, which does not include metallic spring elements that may interfere with imaging, and which has a reduced cross-section. Other problems with the prior art not described above can also be overcome using the teachings of the present invention, as would be readily apparent to one of ordinary skill in the art after reading this disclosure.

SUMMARY OF THE INVENTION

Provided herein are embodiments of various catheters with improved steering and maneuverability. Some of the embodiments include ultrasound imaging transducers.

In one embodiment, a catheter includes an elongated tubular member having a proximal end, a distal end and a lumen extending therebetween (i.e., between the proximal end and the distal end). A plurality of electrical cables, such as coaxial cables are bundled together and located within the lumen of the tubular member. The cross-section of the bundle of cables is substantially ovular or rectangular so as to be preferentially or selectively bendable in approximately two opposite directions. In an embodiment, the catheter includes an ultrasound transducer adjacent the distal end of the tubular member, and the distal end of the plurality of coaxial cables is connected to the ultrasound transducer. In another embodiment, the catheter includes a steering cable that has a first end and a second end. A pulling force applied to the first end causes the tubular member to bend in a first direction, and a pulling force applied to the second end causes the tubular member to bend in a second direction opposite the first direction. In yet another embodiment, a first section of the tubular member adjacent the transducer is more tubular than a second section of the tubular member proximal the first section. The first section of the tubular member can be capable of being bent at a first radius of curvature, and the second section of the tubular member can be capable of being bent at a second radius of curvature, wherein the second radius of curvature can be greater than the first radius of curvature.

In another embodiment, a steerable ultrasound catheter includes an ultrasound transducer array connected to a distal end of a plurality of coaxial cables forming a bundle. The bundle has a proximal end and distal end. The distal end can be connected to the transducer array. The cross-section of the bundle is substantially ovular or rectangular so as to be preferentially or selectively bendable in two approximately opposite directions. The catheter further includes a first cylinder, a second cylinder, and a hollow elongated tubular member. The first cylinder has a proximal end with an opening, a distal end with an opening, and a lumen extending therebetween (i.e., between the proximal end and the distal end). The bundle of coaxial cables is inserted through the opening in the distal end of the cylinder. The cylinder also includes a first aperture and a second aperture, and the two apertures oppose each other. A steering cable is threaded through the opening in the proximal end of the cylinder passing through the lumen of the cylinder, out the first aperture, around an outer circumference of the cylinder, and through the second aperture back into the lumen of the cylinder and back out the opening in the proximal end of the cylinder. The ends of the steering cable may be connected so as to form a single, elongated loop. The second cylinder also has a proximal end with an opening, a distal end with an opening, and a lumen extending therebetween (i.e., between the proximal end and the distal end). The first cylinder is inserted through the opening in the distal end of the second cylinder and the steering cable extends through the lumen of the second cylinder and out the opening at the proximal end of the second cylinder. The hollow elongated tubular member is fitted over the proximal end of the second cylinder and receives the bundle of coaxial cables and the steering cable.

In yet another embodiment, a steerable catheter includes an elongated tubular member having a proximal end, a distal end, and a lumen extending therebetween (i.e., between the proximal end and the distal end). A steering cable having a first section, a second section, and a third section is threaded through the elongated tubular member such that the first and third sections are adjacent one another and are separated from one another at a second section, which forms a loop around the distal end of the elongated tubular member, wherein a first pulling force applied to the first section bends the catheter in a first direction, and a second pulling force applied to the third section bends the catheter in a second direction opposite the first direction. In one embodiment, the first and third sections are intertwined. In another embodiment, the catheter includes a second elongate member within the lumen of the elongated tubular member. The second elongate member also includes a lumen, and the first and third sections of the steering cable are located within that lumen.

An ultrasound catheter is provided herein in yet another embodiment. The ultrasound catheter includes an elongated tubular member having a first section, a second section distal the first section, and third section distal the second section. The first section has a first Shore Durometer hardness. The second section has a second Shore Durometer hardness that is less than the first Shore Durometer hardness. The third section has a third Shore Durometer hardness that is less than the second Shore Durometer hardness. An ultrasound transducer is mounted on the elongated tubular member adjacent the third section. The first section of the tubular member is capable of being bent at a first radius of curvature. The second section of the tubular member is capable of being bent at a second radius of curvature, which is less than the first radius of curvature. The third section of the tubular member is capable of being bent at a third radius of curvature, which is less than the second radius of curvature.

Other embodiments provide methods of imaging an anatomical structure of an individual. The individual can be a human, mammal or other animal. In one embodiment, an ultrasound catheter is provided. The ultrasound catheter includes an elongated tubular member having a proximal end, a distal end and a lumen extending therebetween (i.e., between the proximal end and the distal end). An ultrasound transducer is carried by the tubular member adjacent its distal end. A plurality of coaxial cables is bundled together and located within the lumen of the tubular member. The cross-section of the bundle of cables is substantially ovular or rectangular so as to be preferentially or selectively bendable in two approximately opposite directions. The method can further include making an incision in the individual, inserting the catheter through the incision, and advancing the catheter into the hollow anatomical structure by bending the distal end of the catheter along the longer sides of the ovular or rectangular cross-section of the bundle of cables while pushing the catheter forward with respect to the incision, such as through an artery or vein. The transducer can then be activated to take an image of the hollow anatomical structure.

Embodiments also provided include methods of steering a catheter within a body, which can be a human, mammal or other animal body. In one embodiment, the method includes advancing a catheter within a body. The catheter can include an elongated tubular member having a proximal end, a distal end and a lumen extending therebetween (i.e., between the proximal end and the distal end). A plurality of electrical cables, such as coaxial cables are bundled together and located within the lumen of the tubular member. The cross-section of the bundle of cables is substantially ovular or rectangular so as to be preferentially or selectively bendable in two approximately opposite directions. The method further includes applying a first force to the bundle of cables to cause the distal end of the elongated tubular member to form a bend, and advancing the catheter within the body. A second force can be applied to the bundle of cables to remove the bend in the distal end, wherein the second force is opposite the first force.

Other objects, features and advantages of the embodiments of this disclosure will become apparent from consideration of the following description taken in conjunction with the accompanying drawings and claims.

BRIEF DESCRIPTION OF THE DRAWINGS

FIG. 10 is a further assembly illustration showing an elongate tubular member being guided over the catheter subassembly.

FIG. 11, is a side elevation view of the assembled ultrasound catheter depicted in FIGS. 1, 2, and 4-10.

FIG. 15 is a three-dimensional view of a subassembly of a portion of a steering mechanism used with the subassembly depicted in FIG. 14.

FIG. 15A is a three dimensional view of a flexible tubular member used in the subassembly depicted in FIG. 15.

FIG. 15B is a three dimensional view of a cylinder used in the subassembly depicted in FIG. 15.

FIG. 15C is a three dimensional view of a cylinder used in the subassembly depicted in FIG. 15.

FIG. 15D is a side elevation view of the subassembly depicted in FIG. 15.

DETAILED DESCRIPTION OF THE EXEMPLARY EMBODIMENTS

In this section, a detailed discussion of various embodiments is provided. From the following discussion, skilled artisans readily will recognize numerous modifications, permutations and alterations that may be made to the various specific embodiments described.

Figure 1:
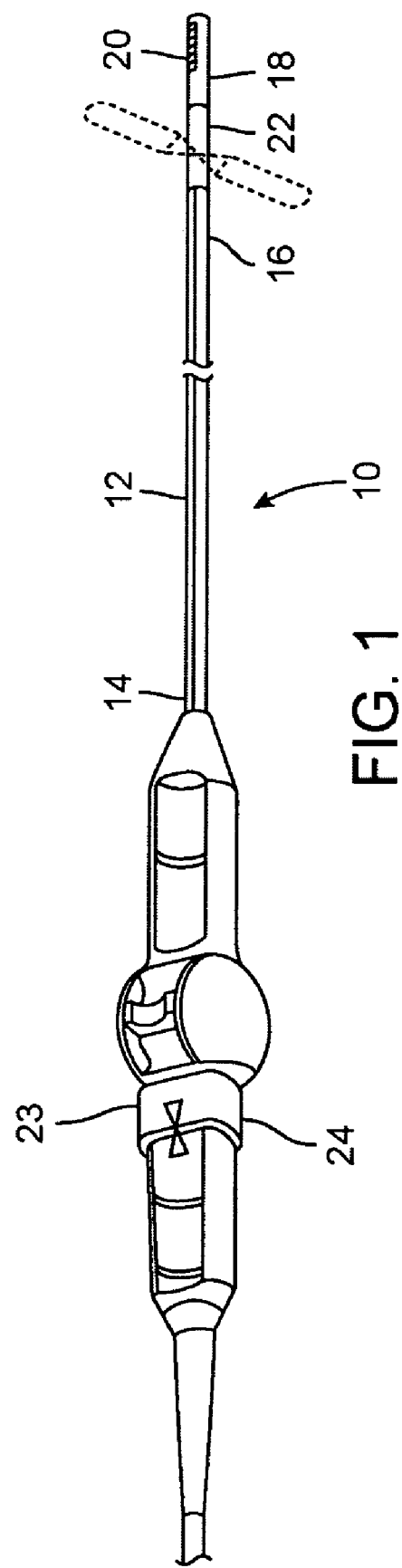
FIG. 1 is a perspective view of an ultrasound catheter with two-way steering.

Referring now to the drawings in detail wherein like reference numerals have been used throughout the various figures to designate like elements, there is shown in FIG. 1 a steerable catheter constructed in accordance with the principles of the present invention and designated generally as 10. For purposes of illustration only, the following description will refer to a steerable ultrasound catheter 10, though other steerable catheters including ablation catheters and electrophysioogy catheters (with or without ultrasound imaging capabilities) are also contemplated. The steerable ultrasound catheter 10 is adapted to be easily maneuvered through the mammalian, in particular human, cardiovascular system and function to perform ultrasound imaging in a manner well known in the art.

The catheter 10 includes an elongated tubular member 12. In one embodiment, the material for the tubular member is extruded polyether block amide of the type sold by Atochem North America, Inc. under the trademark PEBAX. Depending on the intended use of the catheter, the tubular member can be made of PEBAX 7233 having a Shore Durometer hardness of approximately 72 D, PEBAX 7033 having a Shore Durometer hardness of approximately 69 D, PEBAX 6333 having a Shore Durometer hardness of approximately 63 D, PEBAX 5533 having a Shore Durometer hardness of 55 D, PEBAX 4033 having a Shore Durometer hardness of 40 D, PEBAX 3533 having a Shore Durometer hardness of 35 D, or PEBAX 2533 having a Shore Durometer hardness of 25 D. Furthermore, different sections along the length of the tubular member 12 can be made from different grades of PEBAX to give the catheter 10 variable flexibility along its length. The tubular member 12 can also be formed from other materials as well, such as other polymeric materials that have excellent shape retention characteristics. For example, the tubular member 12 can be made of polyethylene, silicone rubber, or plasticized PVC.

Many catheters that are presently used in intravascular applications are about 90 cm in insertable length. The catheter 10 can range from about 80 cm in insertable length to about 120 cm in insertable length. In one embodiment, the catheter 10 is about 90 cm in length. Some applications, such as veterinarian imaging of large animals (e.g., horses), will benefit from a longer insertable length. Thus, the catheter 10, can also be about 100 cm, about 110 cm, about 120 cm, or even longer in length.

Most catheters that are presently used in intravascular applications, particularly those with ultrasound transducers, are at least about 10 French in diameter. The electronics and wires that are made necessary for implementation of ultrasound have made it impractical and expensive to reduce the size of such catheters below about 10 French. The catheter 10 can range from about 6 to about 12 French in diameter. The bundling arrangement of the cables and steering mechanism, described in more detail below, makes it possible to effectively and efficiently reduce the diameter below about 10 French, to about 9 French, about 8 French, about 7 French, or even about 6 French (approximately 2 mm).

Tubular member 12 has a proximal end 14 and a distal end 16. Located at the distal end of the elongated tubular member 12 is an ultrasound transducer 18. The transducer 18 can be formed from an array of individual ultrasound elements such as shown at 20. As is well known in the art, there may be forty-eight or more such ultrasound elements 20 that form the transducer 18. In an embodiment, transducer 18 is a sixty-four element linear phased array ultrasound imaging sensor. One example of an ultrasound transducer that can be incorporated into the catheter 10 is described in more detail in U.S. application Ser. No. 09/263,755 filed on Mar. 5, 1999, and assigned to the assignee of the present application. U.S. application Ser. No. 09/263,755 is incorporated herein by reference in its entirety.

The orientation of the transducer 18, which may determine the direction in which ultrasound is emanated (which in the case of a linear phased array constitutes an imaging plane) can be changed by bending the distal end 16 of the tubular member 12 from a remote location for steering purposes and for allowing for different imaging angles. The manner in which the transducer 18 at the distal end 16 of the catheter 10 is steered is illustrated diagrammatically in FIG. 1 in phantom. The details of how this is accomplished are described more fully below. A portion 22 of the tubular member 12 may be made more flexible than the portions of the tubular member 12 proximal the portion 22, to provide improved catheter maneuverability and to decrease the risk of damage to an anatomical structure, such as a blood vessel or heart chamber during advancement of the catheter tip. By increasing the flexibility of portion 22, the catheter 10 will tend to bend at the proper position. Thus, for example, the Shore Durometer hardness of the material forming portion 22 can be about 35 D to 63 D, or more preferably about 40 D to about 55 D. Different grades of PEBAX as described above, for example, can be used to make portion 22 have the desired flexibility.

Located at the proximal end 14 of the tubular member 12 is a steering mechanism 24. The steering mechanism 24 can be a rotatable control knob, handle or wheel as shown, a slide actuator, or other suitable manipulating member that is mounted in a control handle 23. The steering mechanism 24 controls tension applied to one or more steering cables that extend through the lumen of the tubular member 12 to a point adjacent the distal end thereof for controlling the bending movement of the catheter proximate the transducer 18 as described more fully herein.

Figure 2:
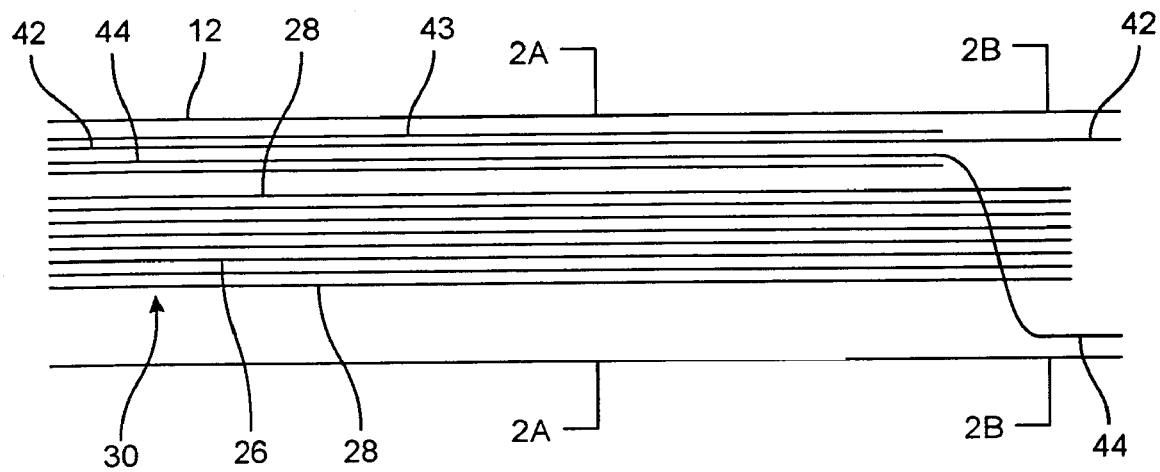
FIG. 2 is a side elevation view of a section of the steerable ultrasound catheter depicted in FIG. 1.

FIG. 2 shows a lateral view of a section of the elongated tubular member 12. The elongated tubular member 12 is hollow and has a lumen extending therethrough. Nested within the lumen of the elongated tubular member 12 is a bundle 30 of electrical cables 26 and a conduit 43 for one or more steering cables. In the illustrated embodiments, the electrical cables 26 are coaxial cables suitable for use with ultrasound transducers. The bundle 30 is formed by bundling together all of the coaxial cables 26 that are necessary to operate the transducer 18. If the transducer 18 is a thirty-two element transducer, then generally thirty-two coaxial cables 26 will form the bundle 30. If the transducer 18 is a forty-eight element transducer, then generally forty-eight coaxial cables 26 will form the bundle 30. If the transducer 18 is a sixty-four element transducer, then generally sixty-four coaxial cables 26 will form the bundle 30, and so on. Accordingly, the catheter can carry a transducer having any number of elements, and is not intended to be limited by the number of elements in the transducer. The bundle 30 will preferably carry a corresponding number of coaxial cables 26 to match the number of elements in the transducer. It should be appreciated, however, that the cross-sectional diameter of the catheter 10 can be reduced by reducing the number of coaxial cables 26 and, correspondingly, the number of elements in the transducer 18. In one embodiment, for example, the transducer 18 can have a sixty-four element parallel drive phased array, which corresponds with a bundle 30 having at least sixty-four coaxial cables 26. It should be appreciated that none of the embodiments described herein are limited by the number of elements in the transducer 18. It should be further appreciated that in ablation and electrophysiology catheter embodiments the electrical cables 26 will be the number and configuration appropriate for connecting the ablation or electrophysiology sensor electrodes to external equipment, and may be coaxial, twisted pair, dual stranded or single stranded electrical conducting cables as appropriate to such applications.

In the embodiment shown in FIG. 2, the coaxial cables 26 are bundled within a protective sheath 28 forming an ovular or rectangular cross-section. The protective sheath 28 may be formed from polyamide or PVC. Further, the bundle 30 can include various types of filler material (not shown), such as Pebax, to provide the catheter 10 with different shape retention and rigidity characteristics. In another embodiment, the coaxial cables are spun together along with one or more filler materials to form a bundle 30 having an ovular or rectangular cross-section.

Figure 2A:
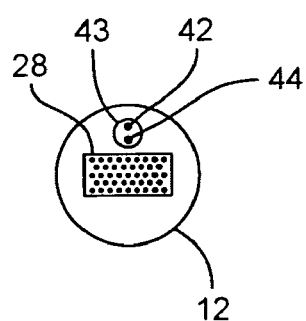
FIG. 2A is a transverse cross-sectional view taken generally along lines 2A-2A in FIG. 2.
Figure 2B:
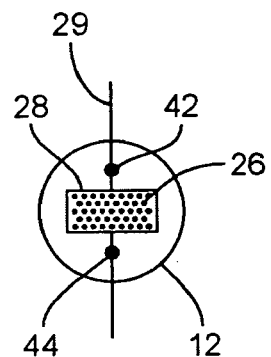
FIG. 2B is a transverse cross-sectional view taken generally along lines 2B-2B in FIG. 2.
Figure 3:
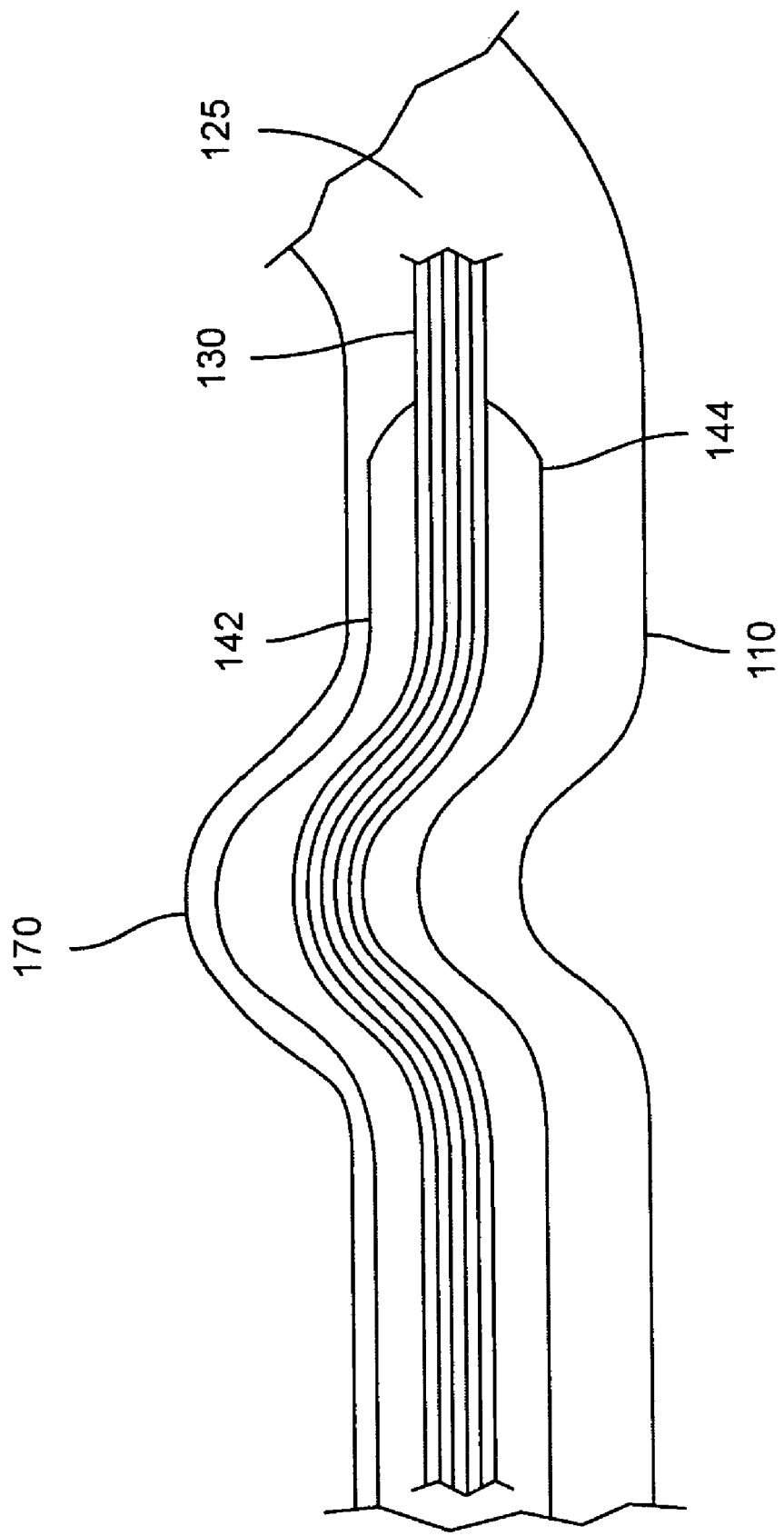
FIG. 3 is a side elevation view of a section of an imaging catheter according to an embodiment showing a kink or bend in a proximal end of the catheter.

As shown in FIGS. 2, 2A, and 2B, a hollow steering cable conduit 43 includes a lumen that carries one or more steering cables 42 and 44. In one embodiment (as shown in FIGS. 2, 2A, and 2B), the steering cables 42 and 44 are nested together along most of the length of the elongated tubular member 12. The advantage of nesting the steering cables together along the length of the elongated tubular member 12 is that a bend in the proximal end of the elongated flexible member 12 will have minimal or no affect on the steering at the distal end of the catheter, which carries the transducer 18. To clarify this point, in FIG. 3, which shows another embodiment, catheter 110 has steering cables 142 and 144 that are at opposite sides of the bundle 130 along the entire length of the bundle 130. As shown in FIG. 3, a kink or bend 170 at any point along the length of the catheter 110, such as at the proximal end, could cause a corresponding bend at the distal end 125 of the catheter 110. This is because the steering cable 142 on the outside of the bend 170 is more displaced by the bend 170 than the steering cable 144 on the inside of the bend 170, causing an unintentional pulling force by the steering cable 142, which causes a corresponding bend at the distal end of the catheter 130. Thus, although the configuration shown in FIG. 3 is operable, further advantages are gained by nesting the steering cables together along most of the length of the elongated tubular member, as shown in FIGS. 2, 2A, and 2B.

Returning to FIGS. 2, 2A, and 2B, near the distal end of the steering cable conduit 43, the steering cables 42 and 44 diverge. Steering cable 42 remains on one side of the bundle 30, while steering cable 44 is threaded around the bundle 30 to the other side thereof. When a pulling force is applied to steering cable 42, the steering cable 142 causes a corresponding pulling force upon the distal end of the bundle 30, thus bending the distal end of the catheter 10 in one direction along a plane identified by line 29 shown in FIG. 2B. In one embodiment, the shape memory filler material incorporated into the bundle 30 retains the bend until a pulling force applied to the steering cable 44 causes an opposite force to be applied to the distal end of the bundle 30, thus causing the catheter 10 to return to its original position or to another position within the same plane 29. In another embodiment, shape memory filler material is not incorporated into the bundle 30, and a pulling force in either direction must be maintained to maintain the bend at the distal end of the catheter 10.

As best seen in FIGS. 2A and 2B, the protective sheath 28 and bundle 30 of coaxial cables 26 has an ovular or rectangular cross section. As a result, the bundle 30 will preferentially or selectively bend in two directions that are approximately 180° opposite each other along the plane identified by line 29 in FIG. 2B. That is, under an applied force, the cable bundle 30 will bend about the longer sides of the oval or rectangle and resist bending along the shorter sides. As shown in FIGS. 2A and 2B, the cable bundle 30 will preferentially or selectively bend up and down. By rotating the catheter 10 about its central axis of rotation, as depicted in FIG. 2C, the catheter 10 can be steered in a left/right direction along the plane identified by line 29.

The ovular or rectangular cross-section of the bundle 30 provides for ample space on the long sides of the rectangle for additional wiring, such as the steering cable conduit 43 and integrated steering cables 42 and 44, working elements or tools, and wiring from additional sensors, such as for example temperature sensors (e.g., a thermister) and/or electrodes (e.g., electrophysiology electrodes). The ovular or rectangular cross-section of the coaxial cable bundle 30 enables catheters with a cross-section diameter as small as about a 9 French, about 7 French, or about 6 French possible.

Figure 2C:
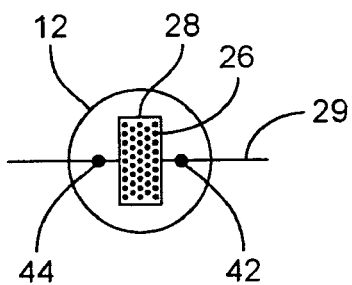
FIG. 2C depicts the catheter shown in FIG. 2B after being rotated by 90°.
Figure 4:
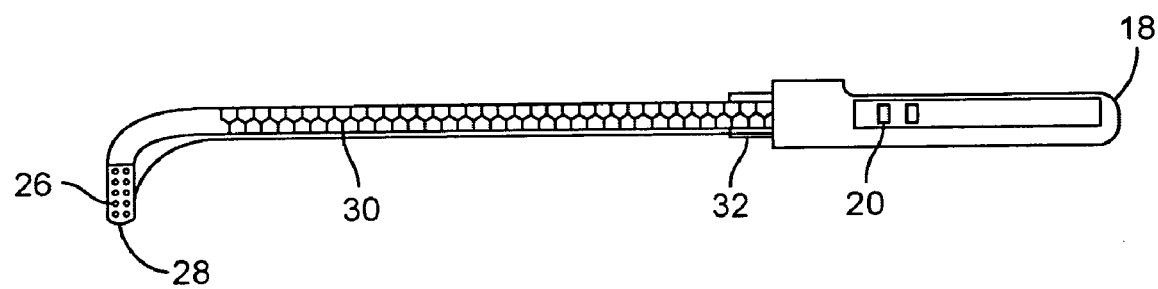
FIG. 4 is a partial, detailed side view of a subassembly showing the transducer and bundled coaxial cables of the ultrasound catheter depicted in FIG. 1.
Figure 5C:
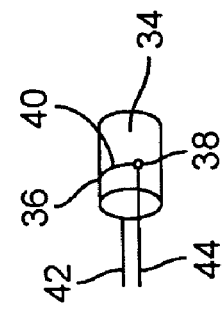
FIG. 5C is a side view of the cylinder depicted in FIG. 5B combined with a steering cable.
Figure 5D:
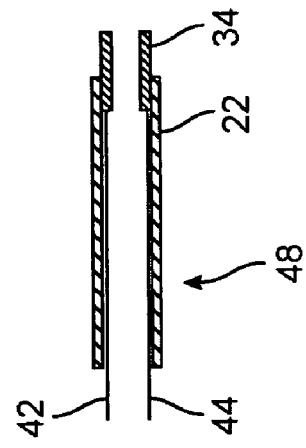
FIG. 5D is a side elevation view of the subassembly depicted in FIG. 5.
Figure 5B:
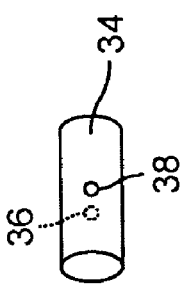
FIG. 5B is a three-dimensional view of a cylinder used in the subassembly depicted in FIG. 5.
Figure 5:
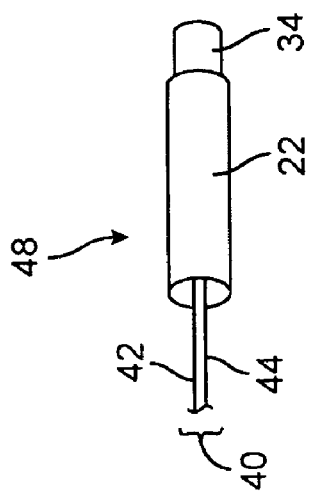
FIG. 5 is a three-dimensional view of a subassembly of a portion of a steering mechanism used with the subassembly depicted in FIG. 4.
Figure 5A:
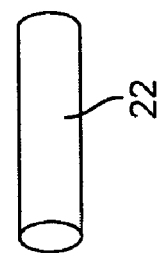
FIG. 5A is a three dimensional view of a flexible tubular member used in the subassembly depicted in FIG. 5.

FIGS. 4-11 depict various stages of constructing the catheter 10 depicted in FIGS. 1, 2, 2A, 2B, and 2C. FIG. 4 is a side view, which illustrates the catheter 10 with the elongated tubular member 12 removed. Each of the transducer elements 20 is connected to its own coaxial cable 26. There may be any number of transducer elements 20 depending on the type of transducer being used, and a corresponding number of coaxial cables 26. In one embodiment, as shown in FIGS. 2A, 2B, and 2C, there are sixty-four separate coaxial cables, each of which is connected to one of sixty-four corresponding elements on the transducer 18. It should be appreciated that none of the embodiments described herein are limited by the number of elements in the transducer 18.

In one embodiment, each of the cables 26 can be contained within a sheath 28, the combination of the cables 26 and sheath 28 forming a bundled group of cables, which is designated generally at 30.

The cable bundle 30 extends from the ultrasound transducer 18 through the elongated tubular member 12 (not shown in FIG. 4, but shown in FIGS. 1, 2, 2A, 2B, 2C, 10 and 11), and through the steering mechanism 24 to be connected to electronic ultrasound imaging equipment through cables coupled to appropriate connectors proximal to the steering mechanism 24 in a manner which is known to those of skill in the art. As is shown in FIG. 4, a supporting pin 32 is connected to the proximal end of the transducer 18 and surrounds the cable bundle 30. The supporting pin 32 may act as the connection between the cable bundle 30 and the transducer 18.

FIGS. 5, 5A, 5B, 5C, and 5D illustrate the bending portion subassembly 48 of the catheter 10, which forms the near-distal end of the cable bundle 30, proximal the transducer 18. A small hollow cylinder 34 is provided that has apertures 36 and 38 formed in the outer wall thereof. According to an embodiment, an elongated steering cable 40 passes through the interior of the cylinder 34, out of the aperture 36, around the outer circumference of the cylinder 34 and back through the aperture 38 to the interior or lumen of the cylinder 34. As a result, two steering cables 42, 44 are essentially formed from the opposite ends 42 and 44 of a single steering cable 40. These two steering cable ends 42 and 44 are lead down through the lumen of the elongated tubular member 12 to the steering mechanism 24, and coupled to the steering mechanism as previously described. The steering mechanism 24 is capable of asserting a pulling force against either of the two ends 42 and 44. When the steering mechanism 24 applies a pulling force on steering cable end 42, the force is applied to cylinder 34 at aperture 36 causing the cylinder to rotate toward steering cable 42. As a result, the force is applied to cylinder 34 at aperture 38 causing the cylinder to rotate toward steering cable 44. As a result, the distal end of the catheter 10 is bent in a first direction towards steering cable 42. When the steering mechanism 24 applies a pulling force on steering cable 44, the distal end of the catheter 10 is bent in a second direction opposite the first direction toward steering cable 44.

In an embodiment, the two steering cable ends 42 and 44 are connected, such as by fusing or tying the ends, forming a single, elongated loop within the catheter 10. In this embodiment, the steering cable elongated loop may be wrapped around a pulley or spindle, for example, in the steering mechanism 24 which can be turned, such as by the operator turning an attached handle or wheel, to exert a pulling force on one side of the elongated loop while letting out the other side of the elongated loop.

In an alternative embodiment (not shown), two separate steering cables are used rather than looping one steering cable over cylinder 34. A distal end of the first steering cable is threaded through the cylinder 34 and out the aperture 36. The distal end of the first steering cable is secured to the outer wall of the cylinder 34 adjacent the aperture 36 by an adhesive, enlarged knot, wrapping it around a screw fastened to the cylinder 34 or other means. A distal end of the second steering cable is threaded through the cylinder 34 and out the aperture 38. The distal end of the second steering cable is secured to the outer wall of the cylinder 34 adjacent the aperture 38 by an adhesive, enlarged knot, wrapping it around a screw fastened to the cylinder 34 or other means. The proximal ends of each of the steering cables are threaded through the lumen of the elongated tubular member 12, out the proximal end of the elongated tubular member 12, and connected to the steering mechanism 24.

The one or more steering cables may comprise a strand, wire, and/or thread, and is preferably made from low profile, durable, non-elastic and non-conducting material. For example, the steering cable(s) can be made of synthetic materials, such as nylon or similar synthetic fibers, or plastics material, such as urethane, Teflon®, Kynar®, Kevlar®, polyethylene, multistranded nylon, or gel-spun polyethylene fibers. For example, the steering cables may be multistranded Spectra® brand nylon line sold as Spiderwire® (10 lbs. test).

Once the steering cable 40 is assembled on the cylinder 34, the flexible tubular member 22 is connected to the cylinder 34, by inserting the proximal end of the cylinder 34 through the distal end of the flexible tubular member 22. Thereafter, an adhesive or fastener (not shown) may be applied to the area where the steering cable 40 abuts the distal end of the flexible tubular member 22 to fix the steering cable 40 and cylinder 34 in place against the flexible tubular member 22. Alternatively, the flexible tubular member 22 and cylinder 34 may be frictionally engaged, with the opposite ends of the steering cable 40 immovably trapped between the lumen of the flexible tubular member 22 and the outer wall of the cylinder 34.

Figure 6:
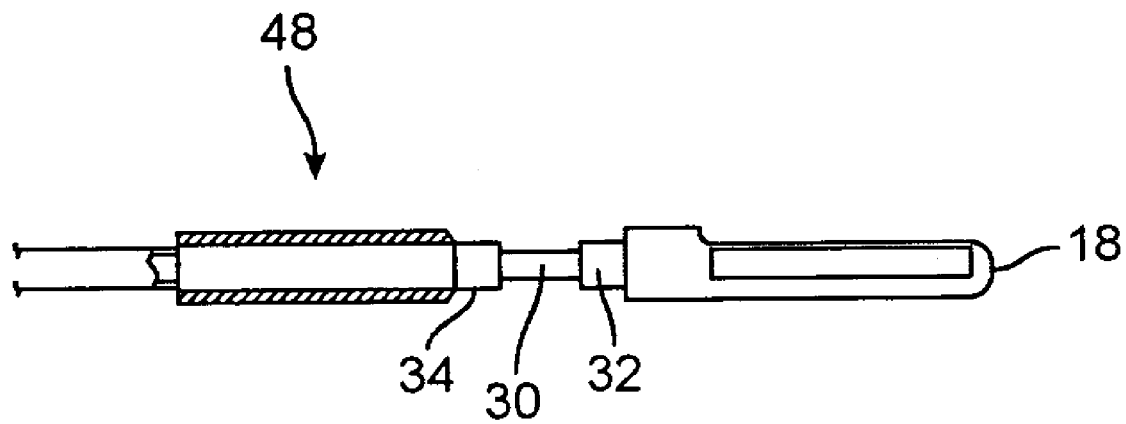
FIG. 6 is a side elevation view showing the addition of the subassembly depicted in FIG. 5 with the subassembly depicted in FIG. 4.
Figure 7:
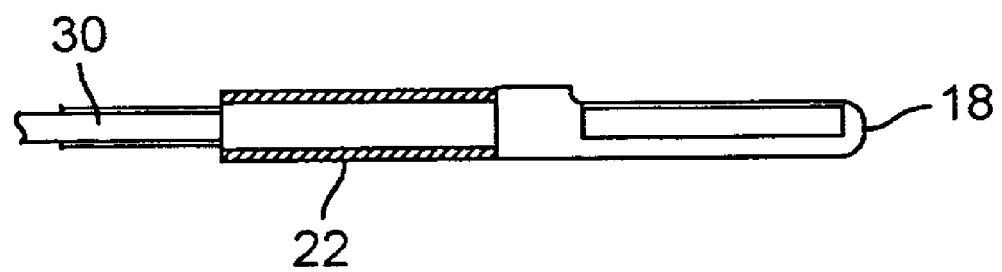
FIG. 7 is a side elevation view showing the final fitting between the subassemblies depicted in FIGS. 4 and 5.

Once the steering cable 40, cylinder 34 and flexible tubular member 22 are combined to form subassembly 48, subassembly 48 is slid over the proximal end of the cable bundle 30 and is moved toward the ultrasound transducer 18 as shown in FIGS. 6 and 7. As the parts are assembled, the distal end of the cylinder 34 fits over the supporting pin 32 and enters the main body of the transducer 18, which may include a recessed fitting to receive the cylinder 34.

During assembly the steering cable end 42 is positioned so that it is aligned with one of the long sides of the ovular or rectangular cable bundle cross-section. The steering cable end 44 is positioned so that it is aligned with the other long side of the ovular or rectangular cable bundle cross-section. This can be achieved by aligning the apertures 36 and 38 with the long sides of the cable bundle 30 when the subassembly 48 is slid over the cable bundle 30 and steering cable ends 42 and 44 and is connected to the transducer 18.

Figure 8:
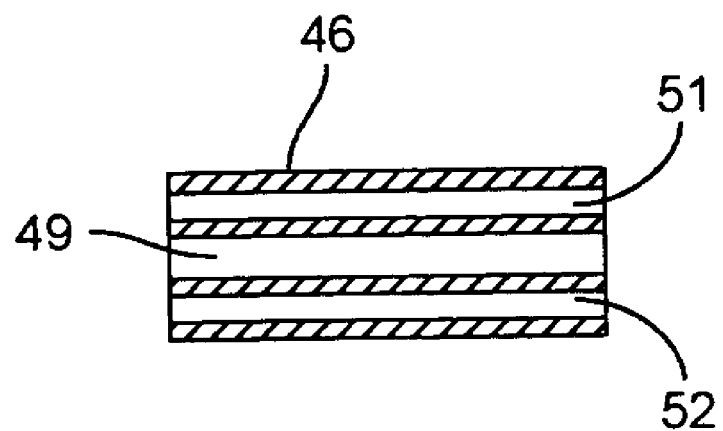
FIG. 8 is a side elevation view of an insert used in the assembly of the catheter depicted in FIGS. 4-7.
Figure 8A:
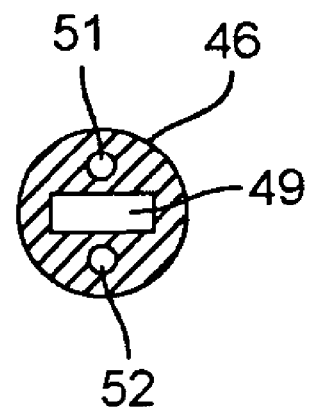
FIG. 8A is a cross-sectional view of the insert depicted in FIG. 8.
Figure 9:
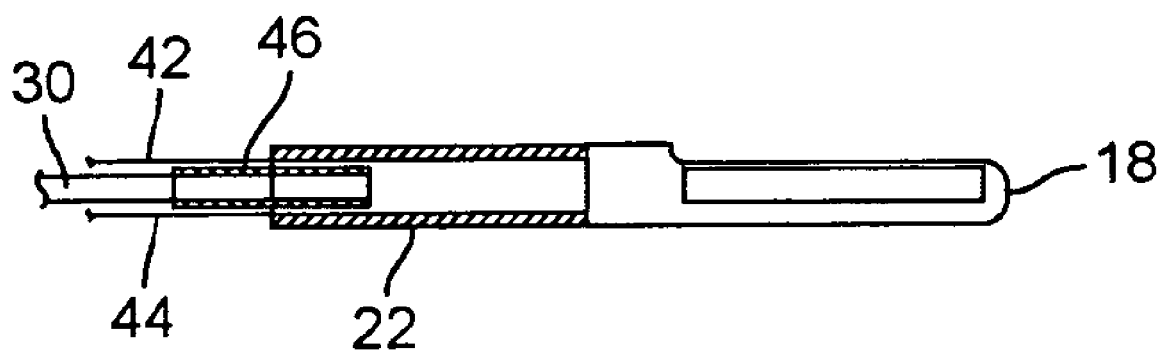
FIG. 9 is a further assembly illustration showing the connection between the insert depicted in FIGS. 8 and 8A and the subassembly depicted in FIG. 7.

In an embodiment shown in FIGS. 8, 8A, and 9, the flexible tubular member 22 has a lumen with a substantially round cross-section. A small flexible tubular insert 46 is slid over the proximal end of the cable bundle 30 and into the lumen of the flexible tubular member 22. The outer diameter of the small flexible tubular insert 46 is just slightly smaller than the diameter of the lumen of the flexible tubular member 22, so that the insert 46 can be nested within the lumen of the flexible tubular member 22. As shown in the cross-sectional view in FIG. 8A, the insert 46 has an ovular or rectangular shaped opening 49 and lumen which is complimentary to the ovular or rectangular shape cross-section of the cable bundle 30. The insert 46 also includes upper and lower axially extending apertures 50 and 52 passing through the length thereof. The apertures run along the longer sides of the ovular or rectangular lumen. Steering cable ends 42 and 44 can be threaded through these apertures 50 and 52 respectively during assembly.

In another embodiment, the lumen of the flexible tubular member 22 has an ovular or rectangular cross-section that matches the ovular or rectangular cross-section of the cable bundle 30. In this embodiment, a separate insert, such as insert 46, is not needed.

As shown in FIGS. 9, 10 and 11, the axial length of the insert 46 is less than the length of the flexible tubular member 22. Thus, when the insert 46 is slid into and nested within the flexible tubular member 22, the proximal end of the insert is distal to the proximal end of the flexible tubular member 22 such that the insert is nested well within the tubular member 22. The flexibile tubular member 22 may be, for example, silicon, Pebax or polyethylene with an outside diameter of about 9 French and about 1 to about 3 inches in length. A cylindrical member 54, similar to the cylinder 34 but without the apertures in the side walls, is guided over the proximal ends of the cable bundle 30 and steering cable ends 42 and 44 and into the lumen of the flexible tubular member 22. The outer diameter of the cylindrical member 54 can be just slightly smaller than the diameter of the lumen of the flexible tubular member 22, so that it can slide into the flexible tubular member 22. The distal end of the cylindrical member 54 is pushed forward until it abuts the proximal end of the insert 46. Once in place, the distal end of the cylindrical member 54 may be secured to the flexible tubular member 22 using an adhesive on the outer wall of the cylindrical member 54 or on the inner luminal wall of the flexible tubular member 22. Alternatively, the cylindrical member 54 may be secured to the inner luminal wall of the flexible tubular member 22 through friction.

As shown in FIGS. 10 and 11, one or more guides 56 and 58 may then be placed around the cable bundle 30 along the length thereof to help support and guide the steering cable ends 42 and 44. The guides 56 and 58 also serve the purpose of keeping the steering cables substantially bundled together along most of their length. Alternatively, or in addition, the steering cable ends may be bundled together in a steering cable conduit along most of their length, and separated only at the distal end of the catheter 10, where the steering cable 40 is threaded through the apertures 50 and 52. If a steering cable conduit is used, the steering cable ends may be threaded into the lumen of the conduit through the distal end of the conduit. The conduit may then be guided forward toward the transducer 18 until it is near the cylinder 54, preferably so as to provide control of the direction of the transducer 18.

The last step of assembly involves the elongated tubular member 12, which forms the outer surface of the catheter 10. The elongated tubular member 12 is guided over the cable bundle 30 and steering cable ends 42 and 44 (or steering cable conduit if one is used). It is pushed forward until the distal end of the elongated tubular member 12 slides over the cylinder 54 and rests against the proximal end of the flexible tubular member 22. The elongated shaft 12 has an outer diameter of about 6 French to about 9 French, and an inner diameter large enough to encompass the cable bundle 30, steering cables 42, 44 and any other included wires (not shown). The elongated tubular member 12 may be secured to the steering portion of the catheter by using an adhesive, compression fit or mechanical collar or latch (not shown) to adhere the distal end of the elongated tubular member 12 to the cylinder 54 or to the proximal end of the flexible tubular member 22.

The embodiment depicted in FIGS. 1-11 shows a catheter with a distal end having a transducer that can be steered by means of steering cables along a single plane in two approximately opposite directions. Steering along any different plane can be accomplished by rotating the distal end of the catheter.

The distal end of the elongated tubular member 12 and the entirety of the flexible tubular member 22 can be made of PEBAX or PVC, for example, with a Shore Durometer hardness of 35, for example. This gives the distal end of the catheter a one inch radius of curvature. The radius of curvature can be increased by using PEBAX with a higher Shore Durometer hardness, making the elongate tubular member 12 and flexible tubular member 22 stiffer. Alternatively, the radius of curvature can be decreased by using PEBAX with a lower Shore Durometer hardness, making the elongate tubular member 12 and flexible tubular member 22 more flexible.

In another embodiment, as shown in FIGS. 12-23, a catheter is provided with four-way steering rather than two-way steering. The steerable ultrasound catheter 200 is adapted to be easily maneuvered through the mammalian (e.g., human) cardiovascular system and to function to perform ultrasound imaging in a manner well known in the art. It should be understood, however, that the steerable features of the present invention could be used with other types of catheters, such as those described further below.

The catheter 200 includes an elongated tubular member 212. In one embodiment, the material for the tubular member is extruded polyether block amide of the type sold by Atochem North America, Inc. under the trademark PEBAX. Depending on the intended use of the catheter, the tubular member can be made of PEBAX 7233 having a Shore Durometer hardness of approximately 72 D, PEBAX 7033 having a Shore Durometer hardness of approximately 69 D, PEBAX 6333 having a Shore Durometer hardness of approximately 63 D, PEBAX 5533 having a Shore Durometer hardness of 55 D, PEBAX 4033 having a Shore Durometer hardness of 40 D, PEBAX 3533 having a Shore Durometer hardness of 35 D, or PEBAX 2533 having a Shore Durometer hardness of 25 D. Furthermore, different sections along the length of the tubular member 212 can be made from different grades of PEBAX to give the catheter 200 variable flexibility along its length. The tubular member 212 can also be formed from other polymeric materials as well, such as those that have excellent shape retention characteristics. For example, the tubular member 212 can be made of polyurethane, silicone rubber, and plasticized PVC.

Tubular member 212 has a proximal end 214 and a distal end 216. Located at the distal end of the elongated tubular member 212 is an ultrasound transducer 218. The transducer 218 can be formed from an array of individual ultrasound elements such as shown at 220. As is well known in the art, there may be forty-eight or more such ultrasound elements 220 that form the transducer 218, such as a sixty-four element linear phased array ultrasound imaging sensor. The orientation of the transducer 218, and thus the imaging plane of a phased array sensor can be changed by bending the distal end 216 of the tubular member 212 in one of four directions from a remote location for steering purposes and for allowing for different imaging angles. The manner in which the transducer 218 at the distal end 216 of the catheter 200 is steered is illustrated diagrammatically in FIG. 12 in phantom. The details of how this is accomplished are described more fully below. The portions 219 and 215 of the tubular member 212 may be made more flexible than the portions of the tubular member 212 proximal the portions 215 and 219, to provide improved catheter maneuverability and to decrease the risk of damage to an anatomical structure, such as a blood vessel or heart chamber during advancement of the catheter tip. By increasing the flexibility of portions 219 and 215, the catheter 200 will tend to bend at the proper positions. Thus, for example, the Shore Durometer hardness of the material forming portions 219 and 215 can be about 35 D to 63 D, or more preferably about 40 D to about 55 D. Different grades of PEBAX as described above, for example, can be used to design portion 219 and 215 to have the desired flexibility.

Located at the proximal end 214 of the tubular member 212 is a steering mechanism 224. The steering mechanism 224 can be two (i.e., one for each plane of steering) rotatable control knobs, handles or wheels as shown, a slide actuators, or other suitable manipulating members that is mounted in a control handle 223. The steering mechanisms 224 control tension applied to two or more steering cables that extend through the lumen of the tubular member 212 to a point adjacent the distal end thereof for controlling the bending movements of the catheter proximate the transducer 218.

To accomplish four-way steering, the principle of using a cable bundle having an ovular or rectangular cross-section is preserved. To achieve four-way steering, the cable bundle is gradually twisted to form a semi-screw configuration to form two regions oriented at an angle to each other.

Figure 13:
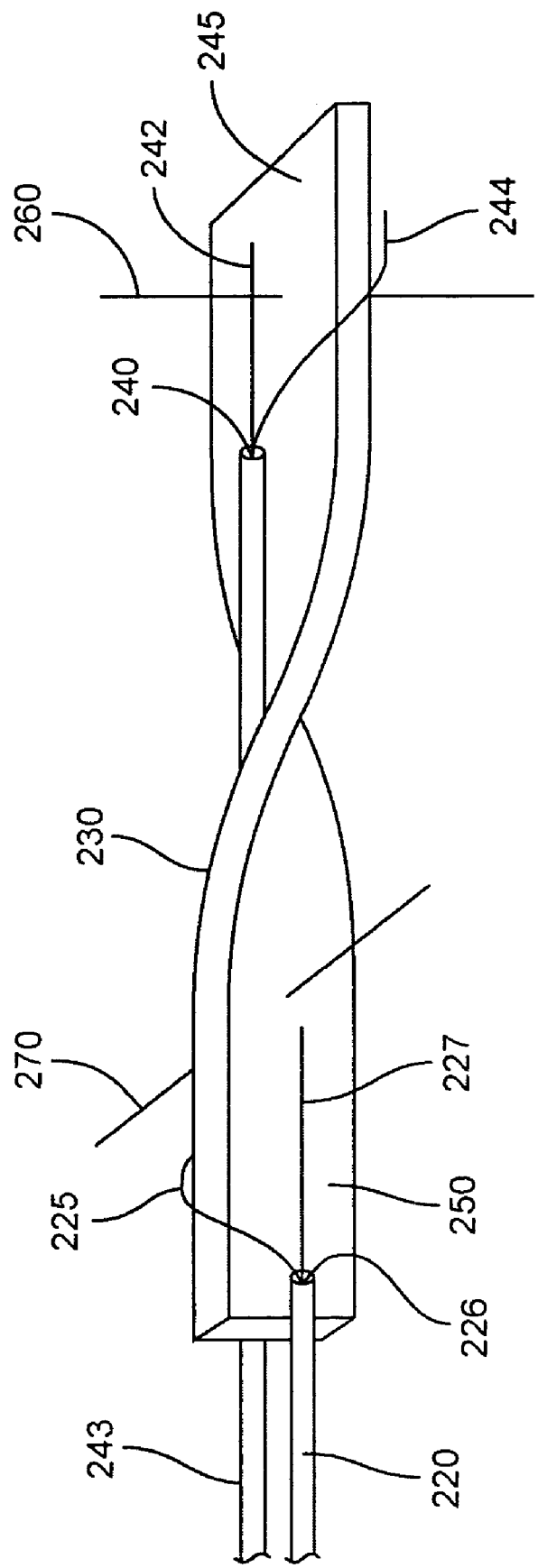
FIG. 13 is a three-dimensional view of a cable bundle steering mechanism according to an embodiment of the present invention.

FIG. 13 depicts the semi-screw configuration of a cable bundle 230 that forms essentially two regions by twisting the cable bundle gradually along its length. In a first region 245, the cable bundle 230 may be steered in a 180° (approximately) arc in plane 260. In a second region 250, the cable bundle 230 may be steered in a 180° (approximately) arc in plane 270. Plane 270 may be approximately perpendicular to plane 260, and consequently region 245 is approximately perpendicular to region 250. This is accomplished by twisting the cable bundle 230 so that it rotates by about 90°. The rotation is gradual and not immediate. Alternatively, the cable bundle 230 may be rotated through less than 90° to provide two planes of rotation oriented at an acute angle to each other. In an embodiment (not shown), the two regions of different bending planes may be formed by forming the cable bundle into ovular or rectangular shapes that have two orientations by shifting the distribution of cables in the bundle between the two regions instead of twisting the cable bundle 230.

Two sets of steering cables are used to steer the catheter. The first set of steering cables may be made of a single steering cable 240 that loops around at the distal end of the catheter and returns to the catheter handle, thus forming two steering cable ends 242 and 244. The steering cable ends include a first steering cable end 242 coupled to one side of the ovular or rectangular bundle 230 at region 245, and a second steering cable end 244 coupled to the other side of the ovular or rectangular bundle 230 at region 245. The manner in which the steering cable ends are coupled to the cable bundle is described in more detail below. A pulling force applied to the steering cable end 242 causes the cable bundle to steer in a first direction toward the steering cable end 242 along plane 260 in a manner similar to that described herein for a two-way steerable catheter. A pulling force applied to the steering cable end 244 causes the cable bundle to steer in a second direction toward the steering cable end 244 along plane 260, which is opposite the first direction.

The second set of steering cables causes the cable bundle 230 to steer along plane 270, which is approximately perpendicular to plane 260. The second set can be made of a single steering cable 226 that loops around at the end of region 250 of the cable bundle 230 and returns to the catheter handle, thus forming two steering cable ends 225 and 227. The steering cable ends include a first steering cable end 225 coupled to one side of the ovular or rectangular bundle 230 at region 250, and a second steering cable end 227 coupled to the other side of the ovular or rectangular bundle 230 at region 240. A pulling force applied to the steering cable end 225 causes the cable bundle to steer in a third direction toward the steering cable 225 along plane 260 in a manner similar to that described herein for a two-way steerable catheter. A pulling force applied to the steering cable 227 causes the cable bundle to steer in a fourth direction toward the steering cable 227 along plane 270, which is opposite the third direction in a manner similar to that described herein for a two-way steerable catheter.

In an embodiment, two steering cable ends 242 and 244 are connected, such as by fusing or tying the ends, forming a first elongated loop within the catheter. Similarly, two steering cable ends 225 and 227 are connected, such as by fusing or tying the ends, forming a second elongated loop within the catheter. In this embodiment, each of the steering cable elongated loops may be wrapped around one of two pulleys or spindles, for example, in the steering mechanism 224 which can be turned, such as with a connected handle or wheel, to exert a pulling force on one side of that elongated loop while letting out the other side of that elongated loop.

In an embodiment, the steering cables are carried by steering cable conduits 243 and 220. Steering cable conduit 243 carries the first set of steering cables, and steering cable conduit 220 carries the second set of steering cables. The advantage of nesting the steering cables together within a steering cable conduit is that a bend in the proximal end of the catheter will have minimal or no affect on the steering at the distal end of the catheter, which carries the transducer 18. This point was discussed in more detail with respect to FIG. 3 above. In accordance with another embodiment, the steering cables can be held together by ties, guides, or other securing means, such as the guides 256 and 258 shown in FIG. 22.

The steering cables may comprise a strand, wire, and/or thread, and is preferably made from low profile, durable, non-elastic and non-conducting material. For example, the steering cable(s) can be made of synthetic materials, such as nylon or similar synthetic fibers, or plastics material, such as urethane, Teflon®, Kynar®, Kevlar®, polyethylene, multi-stranded nylon, or gel-spun polyethylene fibers. For example, the steering cables may be multistranded Spectra® brand nylon line sold as Spiderwire® (10 lbs. test).

Figure 14:
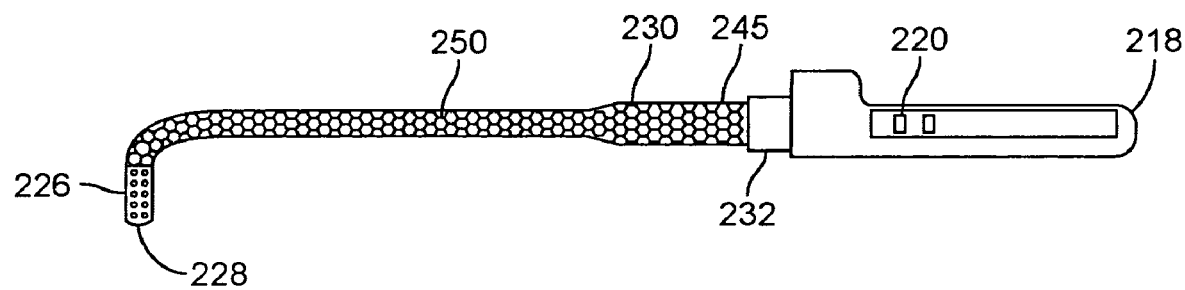
FIG. 14 is a partial, detailed side view of a subassembly showing the cable bundle depicted in FIG. 13 combined with a transducer.

FIGS. 14-23 depict various stages of constructing a catheter with four way steering. FIG. 14 is a side view illustrating the naked catheter with its cable bundle 230 exposed. The ultrasound transducer 218 is at the distal end of the catheter. Each of the transducer elements 220 is connected to its own coaxial cable 226. There may be any number of transducer elements 220 depending on the type of transducer being used, and a corresponding number of coaxial cables 226. In one embodiment, there are sixty-four separate coaxial cables, each of which is connected to one of sixty-four corresponding elements on the transducer 218. It should be appreciated that none of the embodiments described herein are limited by the number of elements in the transducer 218.

In one embodiment, each of the cables 226 can be contained within a sheath 228, the combination of the cables 226 and sheath 228 forming a bundled group of cables, which is designated generally at 230.

The cable bundle 230 extends from the ultrasound transducer 218 through the elongated tubular member 212 (not shown in FIG. 14, but shown in FIGS. 22 and 23), and through the steering mechanism 224 to be connected to electronic ultrasound imaging equipment through cables coupled to appropriate connectors proximal to the steering mechanism in a manner which is known to those of skill in the art.

The cable bundle 230 is shown in greater detail in FIG. 13. Region 245 of the cable bundle 230 is coupled to the transducer 218. The cable bundle 230 spins gradually so that the cable bundle 230 rotates a total of approximately 90°, for example, to form region 250, which is approximately perpendicular to region 245. Region 250 is coupled to the handle 223.

A supporting pin 232 is connected to the proximal end of the transducer 218 and surrounds the cable bundle 230 at region 245. The supporting pin 232 may act as the connection between the cable bundle 230 and the transducer 218.

Figure 12:
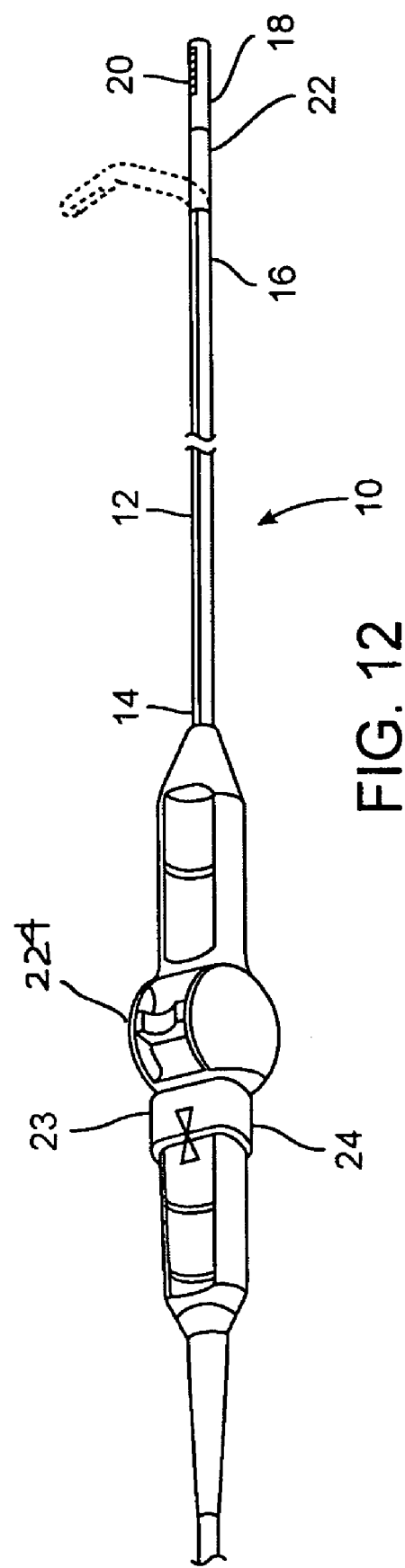
FIG. 12 is a perspective view of an ultrasound catheter with four-way steering.

FIGS. 15, 15A, 15B, 15C, and 15D illustrate the bending portion subassembly 222 of the catheter, which forms the near-distal end of the cable bundle 230, proximal the transducer 218. A small hollow cylinder 234 is provided that has apertures 236 (shown in phantom in FIG. 15B) and 238 formed in the outer wall thereof. According to an embodiment, a single elongated steering cable 240 passes through the interior of the cylinder 234, out of the aperture 236, around the outer circumference of the cylinder 234 and back through the aperture 238 to the interior or lumen of the cylinder 234. As a result, two steering cables 242, 244 are essentially formed from the opposite ends 242 and 244 of the steering cable 240. The two steering cables 242, 244 can be brought to the same side of the oval/rectangle by pulling one of the steering cables over the short side of the oval/rectangle and next to the other steering cable. For example, as shown in FIG. 12, steering cable end 244 can be guided over the short side of the ovular or rectangular cable bundle 230 and brought to the opposite long side of the oval or rectangular cable bundle 230 to join the other steering cable end 242. The steering cable ends 242 and 244 may be kept adjacent the long side of the ovular or rectangular cable bundle 230 along its length, even as the cable bundle rotates. This placement adjacent one of the long sides of the cable bundle provides the advantage of minimizing the ultimate diameter of the catheter. The two steering cable ends 242 and 244 may be lead down adjacent one of the long sides of the cable bundle 230, through the lumen of the elongated tubular member 212 to the steering mechanism 224, and coupled to the steering mechanism 224. The steering mechanism 224 is capable of asserting a pulling force against either of the two ends 242 and 244. When the steering mechanism 224 applies a pulling force on steering cable end 242, the distal end of the catheter is bent in a first direction towards steering cable 242 in a manner similar to that described herein for a two-way steerable catheter. When the steering mechanism 224 applies a pulling force on steering cable 244, the distal end of the catheter is bent in a second direction opposite the first direction toward steering cable 244 in a manner similar to that described herein for a two-way steerable catheter. In this manner, the ultrasound transducer can be steered in a 180° (approximately) arc.

In an alternative embodiment (not shown), two separate steering cables are used rather than looping one steering cable over cylinder 234. A distal end of the first steering cable is threaded through the cylinder 234 and out the aperture 236. The distal end of the first steering cable is secured to the outer wall of the cylinder 234 adjacent the aperture 236 by an adhesive, enlarged knot, wrapping it around a screw fastened to the cylinder 34 or other means. A distal end of the second steering cable is threaded through the cylinder 234 and out the aperture 238. The distal end of the second steering cable is secured to the outer wall of the cylinder 234 adjacent the aperture 238 by an adhesive, enlarged knot, wrapping it around a screw fastened to the cylinder 34 or other means. The proximal ends of each of the steering cables are threaded through the lumen of the elongated tubular member 212, out the proximal end of the elongate tubular member 212, and connected to the steering mechanism.

Once the steering cable 240 is assembled on the cylinder 234, the flexible tubular member 222 is connected to the cylinder 234, by inserting the proximal end of the cylinder 234 through the distal end of the flexible tubular member 222. Thereafter, an adhesive or fastener may be applied to the area where the steering cable 240 abuts the distal end of the flexible tubular member 222 to fix the steering cable 240 and cylinder 234 in place against the flexible tubular member 222. Alternatively, the flexible tubular member 222 and cylinder 234 may be frictionally engaged, with the opposite ends of the steering cable 240 immovably trapped between the lumen of the flexible tubular member 222 and the outer wall of the cylinder 234.

Figure 16:
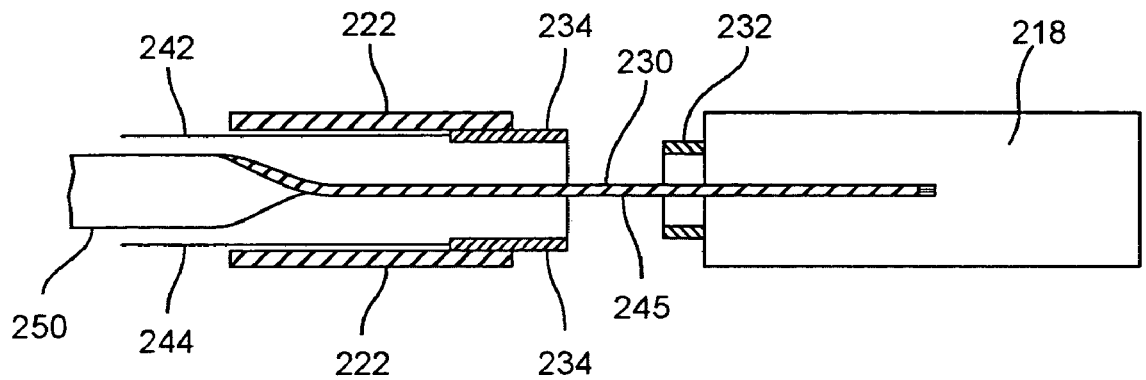
FIG. 16 is a side elevation view showing the addition of the subassembly depicted in FIG. 14 with the subassembly depicted in FIG. 15.
Figure 17:
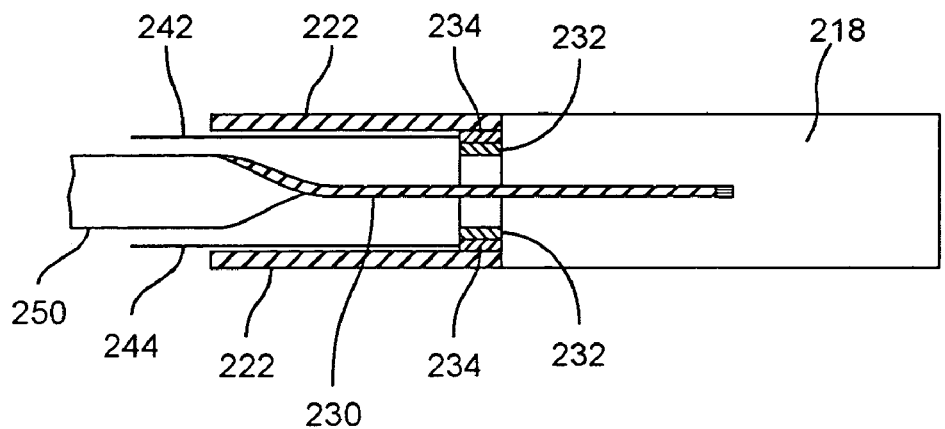
FIG. 17 is a side elevation view showing the final fitting between the subassemblies depicted in FIGS. 14 and 15.

Once the steering cable 240, cylinder 234 and flexible tubular member 222 are combined to form subassembly 248, subassembly 248 is slid over the proximal end of the cable bundle 230 and is moved toward the ultrasound transducer 218 as shown in FIGS. 16 and 17. The lumens of both the flexible tubular member 222 and the cylinder 234 may be round and are both large enough to allow the cable bundle to pass therethrough. As the parts are assembled, the distal end of the cylinder 234 fits over the supporting pin 232 and enters the main body of the transducer 218, which includes a recessed fitting to receive the cylinder 234.

The steering cable end 242 is positioned so that it is aligned with one of the long sides of the ovular or rectangular cable bundle cross-section at region 245 of the cable bundle 230. The steering cable end 244 is positioned so that it is aligned with the other long side of the ovular or rectangular cable bundle cross-section at region 245 of the cable bundle 230. This can be achieved by aligning the apertures 236 and 238 with the long sides of the cable bundle 230 when the subassembly 248 is slid over the cable bundle 230 and steering cable ends 242 and 244 and is connected to the transducer 218.

Figure 18:
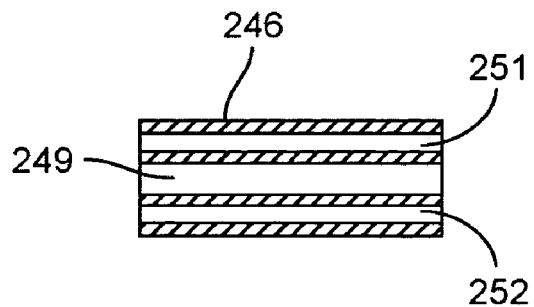
FIG. 18 is a side elevation view of an insert used in the assembly of the catheter depicted in FIGS. 12-16.
Figure 18A:
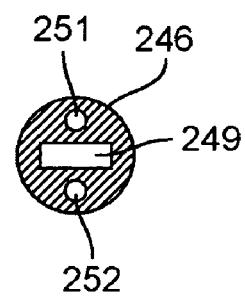
FIG. 18A is a cross-sectional view of the insert depicted in FIG. 18.
Figure 19:
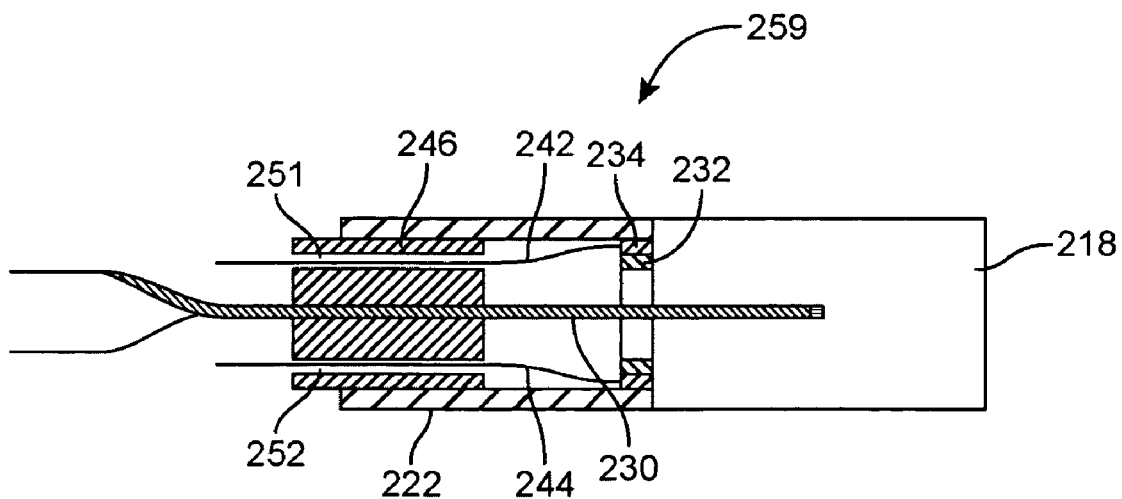
FIG. 19 is a further assembly illustration showing the connection between the insert depicted in FIGS. 18 and 18A and the subassembly depicted in FIG. 17.
Figure 19A:
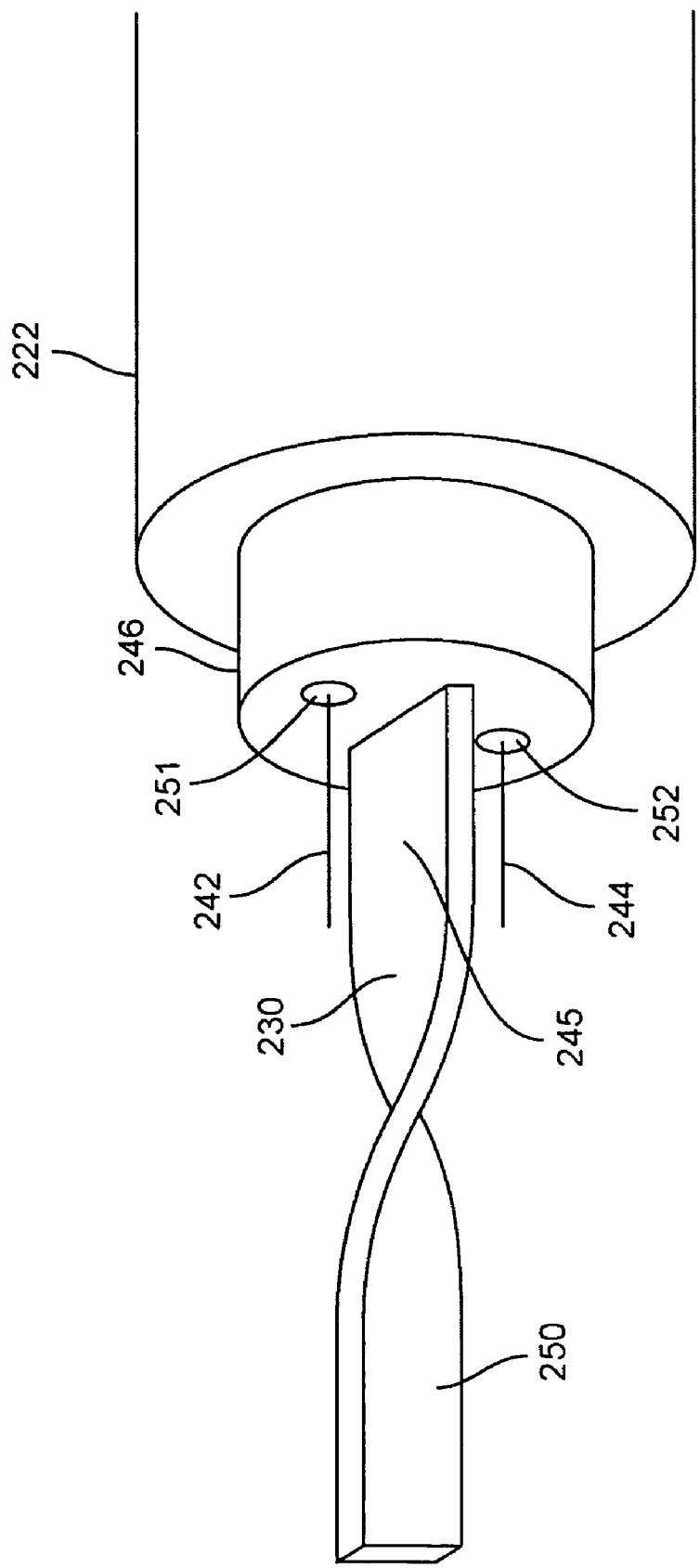
FIG. 19A is a three dimensional view of the assembly depicted in FIG. 19.

In an embodiment shown in FIGS. 18, 18A, 19, and 19A, the flexible tubular member 222 has a lumen with a substantially round cross-section. A small flexible tubular insert 246 with a lumen having an ovular or rectangular cross-section is provided. The insert 246 includes a lumen 249 that has a cross-section that is slightly larger than the cross-section of the cable bundle 230, such that the cable bundle 230 fits snugly into the lumen 249. The tubular insert 246 also includes a first steering cable port 251 and a second steering cable port 252. The steering ports run along the longer sides of the ovular or rectangular lumen 249 as shown in FIGS. 18A and 19A. This configuration ensures that the distal end of the steering cables 242 and 244 are aligned with the longer sides of the ovular or rectangular cross-section of the cable bundle 230. The proximal end of steering cable 242 is threaded into port 251, and the proximal end of steering cable 244 is threaded into port 252. Region 250 of the cable bundle 230 is inserted into the ovular or rectangular lumen 249 of the tubular insert 246. Region 250 is perpendicular to region 245, which is the final resting place of the insert. Therefore, the insert is slid over the proximal end of the cable bundle 230, threaded over the gradually twisted portion of the cable bundle 230 and into the lumen of the flexible tubular member 222. Because of the twist in the cable bundle 230, the insert 246 has rotated by about 90°. The outer diameter of the small flexible tubular insert 246 is just slightly smaller than the diameter of the lumen of the flexible tubular member 222, so that the insert 246 can be nested within the lumen of the flexible tubular member 222 when the subassembly 259 is completed.

In another embodiment, the lumen of the flexible tubular member 222 has an ovular or rectangular cross-section that correspond to the ovular or rectangular cross-section of the cable bundle 230. In this embodiment, a separate insert, such as insert 246, is not needed.

Figure 21:
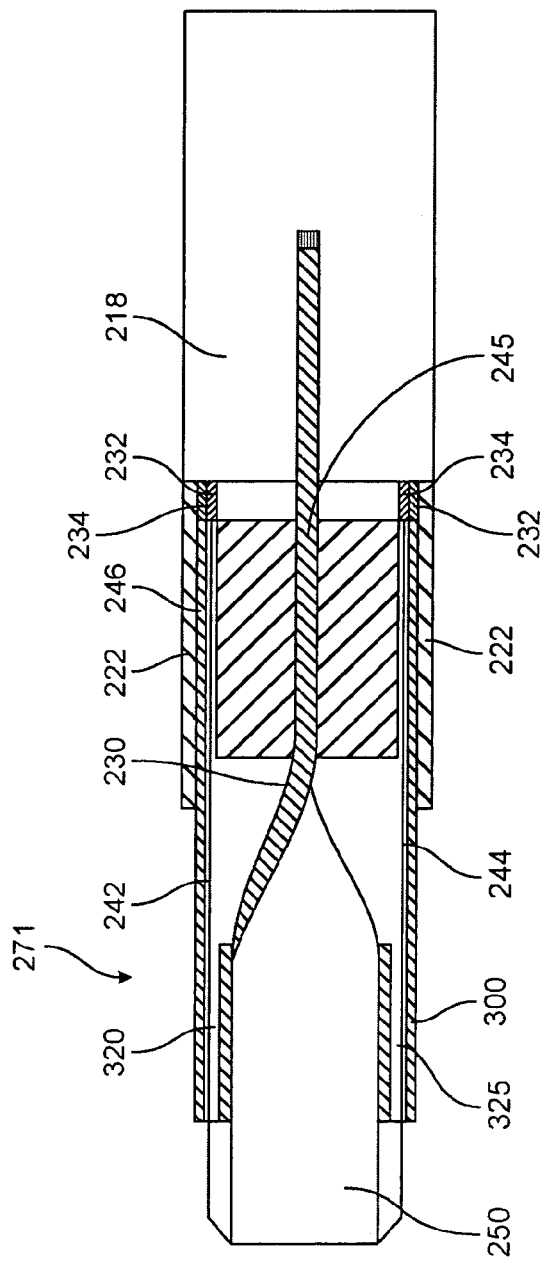
FIG. 21 is a side elevation view of the insert assembled with the subassembly depicted in FIG. 19.

As shown in FIGS. 19 and 21, the axial length of the insert 246 is less than the length of the flexible tubular member 222. Thus, when the insert 246 is slid into and nested within the flexible tubular member 222, the proximal end of the insert is distal to the proximal end of the flexible tubular member 222 such that the insert is nested well within the tubular member 222. The flexible tubular member 222 may be, for example, silicon, Pebax or polyethylene with an outside diameter of about 9 French and about 1 to about 3 inches in length.

Figure 20A:
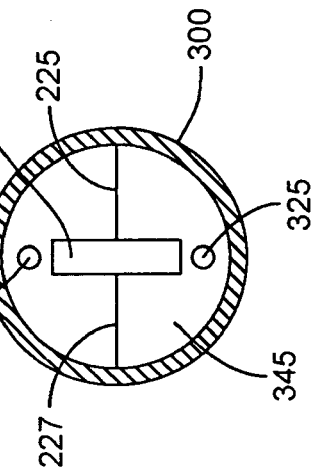
FIG. 20A is a three dimensional view of the insert depicted in FIG. 20 taken from a distal end.
Figure 20C:
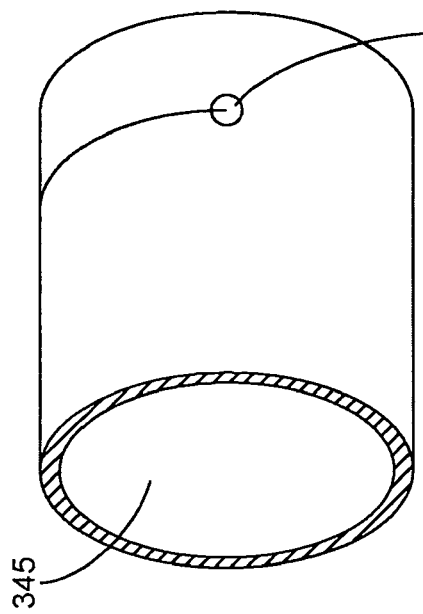
FIG. 20C is a bottom view of the insert depicted in FIG. 20.
Figure 20:
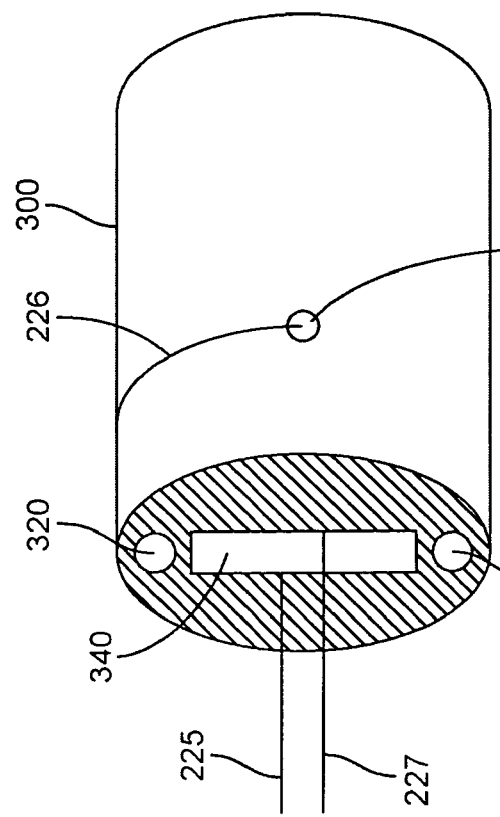
FIG. 20 is a three dimensional view taken from a proximal end of an insert and steering cable ends that are used in the assembly of the catheter depicted in FIGS. 12-19A.
Figure 20B:
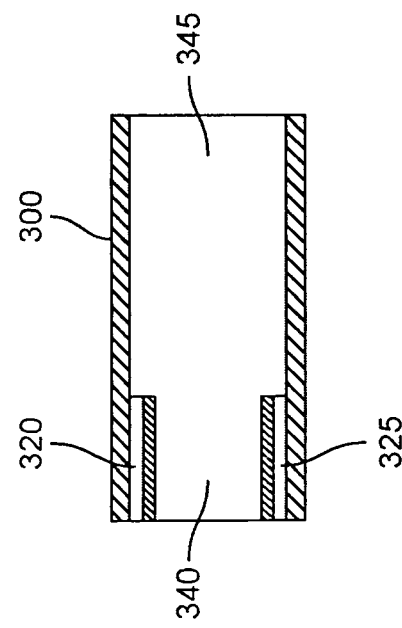
FIG. 20B is a side elevation view of the insert depicted in FIG. 20.

The space between the proximal ends of the flexible tubular member 222 and insert 246 is intended to receive a second insert 300, which is depicted in FIGS. 20, 20A, and 20B. The second insert 300 has an outer cylindrical shape that fits snuggly into the lumen of tubular member 222. The proximal end of the insert 300 has an opening 340 with an ovular or rectangular cross-section. Steering cable ports 320 and 325 are adjacent the shorter sides of the oval or rectangular opening 340. The distal end of the insert 300, as shown in FIG. 20A, has a cylindrical opening 345. The insert 300 also includes apertures 330 and 335, which are on opposite sides of the insert 300.

Apertures 330 and 335 are openings that lead from the outer wall of the insert into the inner core of the insert. According to an embodiment, an elongated steering cable 226 passes through opening 340 and into the interior core of the insert 330, out of the aperture 335, around the outer circumference of the cylindrical insert 300, back through the aperture 330 to the interior or lumen of the cylinder 34, and back out the opening 340. As a result, two steering cables are essentially formed from the opposite ends 225 and 227 of the steering cable 226. These two steering cable ends 225 and 227 are lead down through the lumen of the elongated tubular member 212 to the steering mechanism 224, and coupled to the steering mechanism 224. The steering mechanism 224 is capable of asserting a pulling force against either of the two ends 225 and 227. When the steering mechanism 224 applies a pulling force on steering cable end 225, the distal end of the catheter is bent in a third direction towards steering cable 225 in a manner similar to that described herein for a two-way steerable catheter. When the steering mechanism 224 applies a pulling force on steering cable 227, the distal end of the catheter is bent in a fourth direction opposite the third direction toward steering cable 227 in a manner similar to that described herein for a two-way steerable catheter.

In an embodiment, two steering cable ends 242 and 244 are connected, such as by fusing or tying the ends, forming a first elongated loop within the catheter. Similarly, two steering cable ends 225 and 227 are connected, such as by fusing or tying the ends, forming a second elongated loop within the catheter. In this embodiment, each of the steering cable elongated loops may be wrapped around one of two pulleys or spindles, for example, in the steering mechanism 224 which can be turned, such as with a connected handle or wheel, to exert a pulling force on one side of that elongated loop while letting out the other side of that elongated loop.

In an alternative embodiment (not shown), two separate steering cables are used rather than looping one steering cable over insert 300. A distal end of the first steering cable is threaded through the opening 340 of the insert 300 and out the aperture 335. The distal end of the first steering cable is secured to the outer wall of the insert 300 adjacent the aperture 335 by an adhesive, fastener, enlarged knot, wrapping it around a screw fastened to the cylinder 34 or other means. A distal end of the second steering cable is threaded through the opening 340 of the insert 300 and out the aperture 330. The distal end of the second steering cable is secured to the outer wall of the insert 300 adjacent the aperture 330 by an adhesive, fastener, enlarged knot, wrapping it around a screw fastened to the cylinder 34 or other means. The proximal ends of each of the steering cables are threaded through the lumen of the elongated tubular member 212, out the proximal end of the elongated tubular member 212, and connected to the steering mechanism.

Figure 21A:
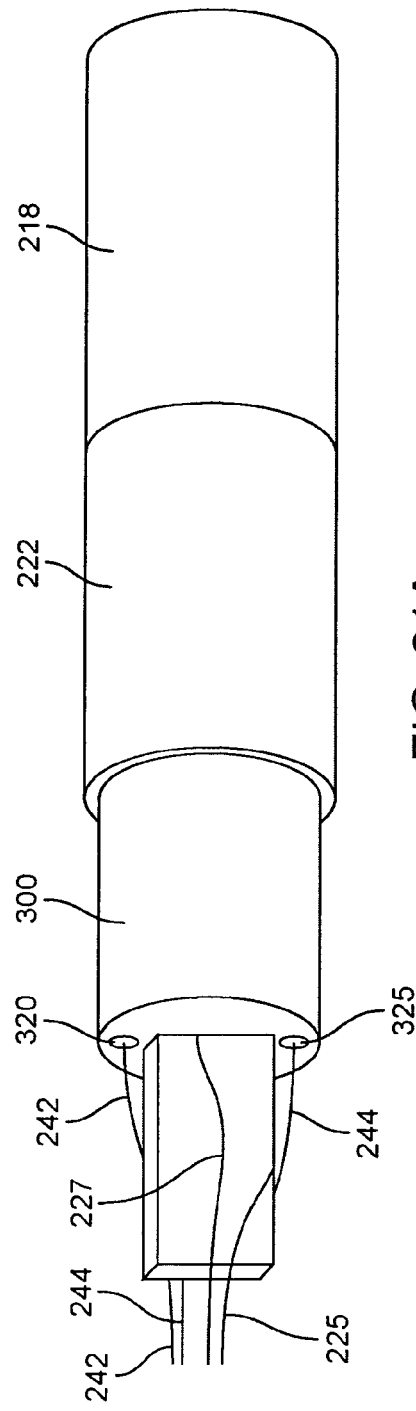
FIG. 21A is a three-dimensional view of the device depicted in FIG. 21.

Once the steering cable 226 is integrated with the insert 300, the insert 300 is ready to be combined with subassembly 259. FIGS. 21 and 21A show this step of the assembly. The steering cables 242 and 244 are threaded through the distal end 345 of the insert 300 and through steering cable ports 320 and 325 respectively. The region 250 of the cable bundle 230 is inserted into the distal end of the insert 300. The insert 300 is guided over the cable bundle 230, which slides through the ovular or rectangular portal 340 of the insert 300. The insert 300 is pushed toward the ultrasound transducer 218 until the distal end 345 of the insert 300 enters the lumen of the flexible tubular member 222 and abuts the proximal end of the insert 246. The insert 300 can be secured against the insert 246 by using an adhesive to bind the outer wall of the insert 300 to the lumen of the flexible tubular member 222 or by adhering the distal end of the insert 300 to the proximal end of the insert 246.

As shown in FIG. 21A, the steering cables 242 and 244 exit their respective ports 320 and 325 and are guided to one of the long sides of the ovular or rectangular cable bundle 230. They remain on that side of the cable bundle 230 proximally along the length of the catheter until they are connected to the steering mechanism 224. Steering cables 225 and 227 exit through the ovular or rectangular opening 340 of the insert 300. Steering cable 225 exits adjacent one of the longer sides of the ovular or rectangular cable bundle 230, and steering cable 227 exits adjacent the opposite side of the ovular or rectangular cable bundle 230. Steering cable 225 is wrapped around the cable bundle to the same side of the cable bundle 230 as steering cable 227. Thereafter, the two steering cables 225 and 227 remain adjacent one another and on the same side of the ovular or rectangular cable bundle 230 proximally along the length of the catheter until they are connected to the steering mechanism 224.

Figure 22:
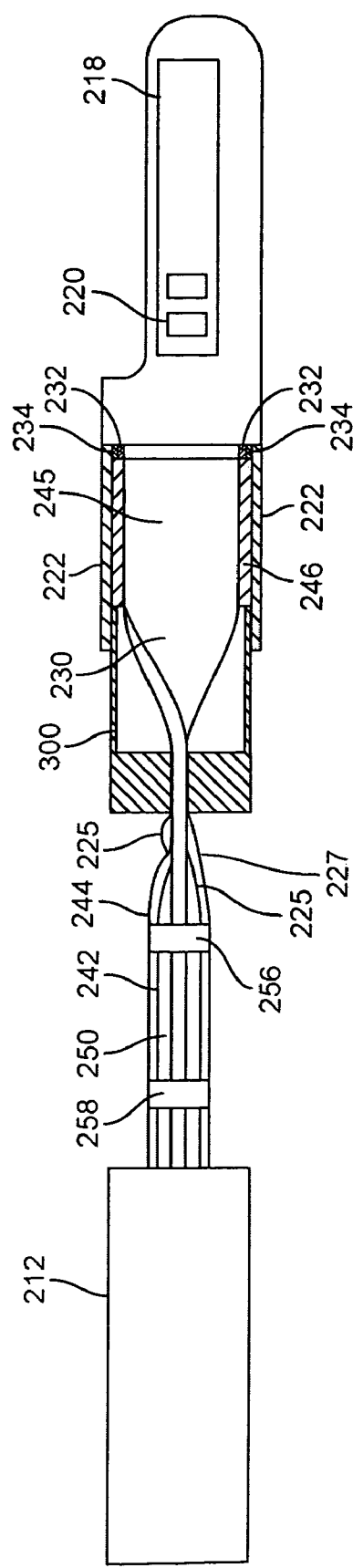
FIG. 22 is a side elevation view of the catheter depicted in FIGS. 12-20A.
Figure 23:
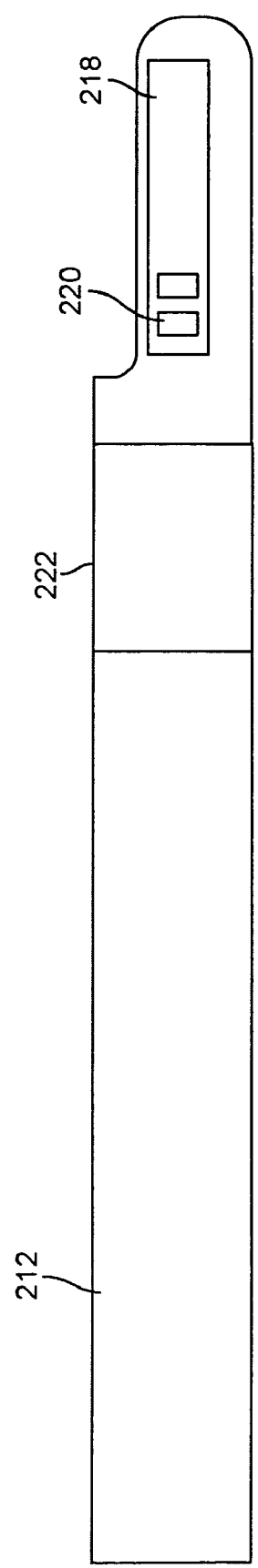
FIG. 23 is a side elevation view of an assembled ultrasound catheter with four-way steering.

FIG. 22 shows the final step of assembly in which the elongated tubular member 212, which forms the outer surface of the catheter, is guided into place. The distal end of the elongated tubular member 212 is threaded over the steering cables and the cable bundle 230 and pushed toward the ultrasound transducer 218 until the distal end rests against the proximal end of the flexible tubular member 222. The elongated tubular member 212 has an outer diameter of about six French to about nine French, and an inner diameter large enough to encompass the cable bundle 230, steering cables 225, 227, 242, 244, and other associated wires. The elongated tubular member 212 may be secured to the steering portion of the catheter by using an adhesive, fastener, compression fit or other means to adhere the distal end of the elongated tubular member 212 to the insert 300 or to the proximal end of the flexible tubular member 222.

The steering cables can be secured in place along the long sides of the cable bundle 230 by using bundling guides 256 and 258. Alternatively, or in addition, the steering cable ends can be bundled in steering cable conduits along most of their length, and separated only at the distal end of the catheter in the steering portion. FIG. 13, for example, shows steering cables 225 and 227 bundled together in steering cable conduit 220, while steering cables 242 and 244 are bundled together in steering cable conduit 243. This may be accomplished by threading the proximal ends of the steering cables into the lumens of the conduits through the distal ends of the conduits. The conduits can then be guided forward toward the transducer 18 until they are near the insert 300.

Figure 24:
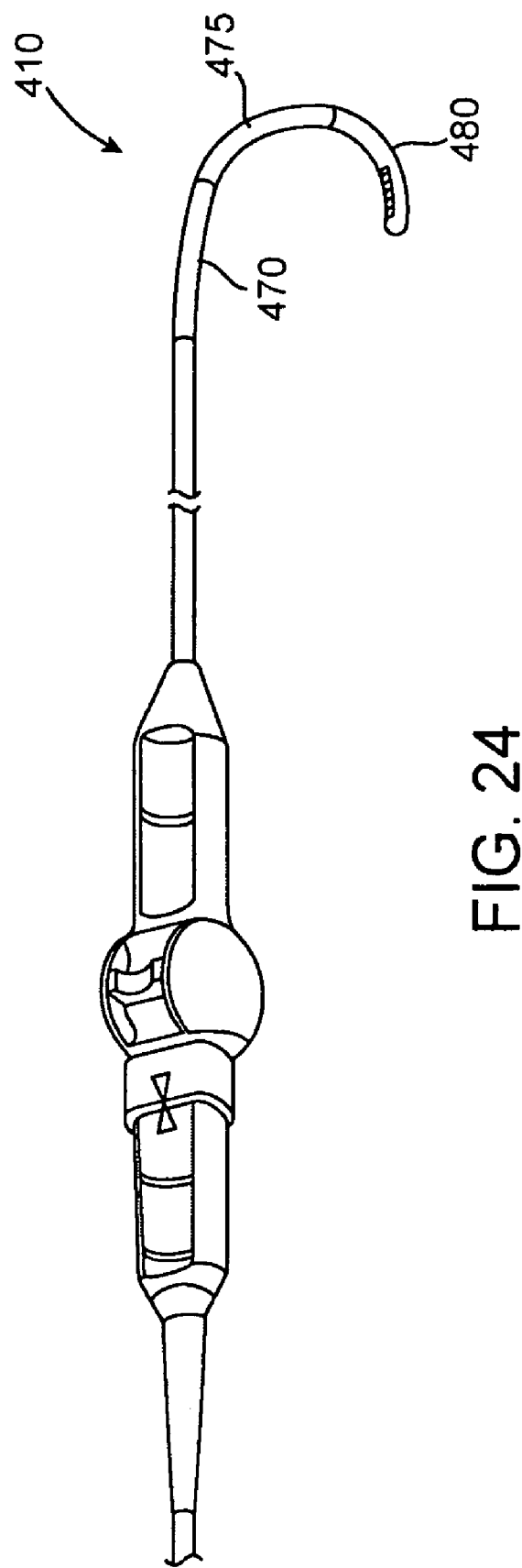
FIG. 24 is a side view of a multi-durometer ultrasound catheter.

Turning to FIG. 24, an imaging catheter 400 is shown with multiple regions of curvature for improved maneuverability. The catheter 400 can be similar in construction to either of catheters 10 and 200 shown in FIGS. 1-11 and 12-23 respectively with one exception. The elongate tubular member 412 of catheter 400 has two, three, four or more separate sections, each being made of a material having a different Shore Durometer hardness and each having a different radius of curvature for improved maneuverability.

In one embodiment, elongate tubular member 412 has three separate sections: a first section 470 having a first radius of curvature; a second section 475 having a second radius of curvature, which is less than the first radius of curvature; and a third section 480 having a third radius of curvature, which is less than the second radius of curvature. The Pebax Shore Durometer typically changes from about 75 D in the first region for good pushability to about 63 D in the second region and about 55 D to about 35 D in the third region for good bendability, steerability or tracking, as the case may be. The catheter also includes a cable bundle 430 having an ovular or rectangular cross-section for purposes of improved steering characteristics and diameter reduction. The cable bundle 430 also serves the function of reinforcement and enhances the ability of the catheter shaft to transmit torque from the handle to the distal end of the device and to elastically bend around curves without kinking or collapsing. In an embodiment, the three interconnecting sections, forming a multi-durometer shaft, is assembled by press fitting the sections as interlocking sleeves.

The present invention has been described above in terms of one or more presently preferred embodiments so that an understanding of the present invention can be conveyed. There are, however, many configurations for steerable ultrasound catheters not specifically described herein but with which the present invention is applicable. The present invention should therefore not be seen as limited to the particular embodiments described herein, but rather, it should be understood that the present invention has wide applicability with respect to steerable ultrasound catheters, systems, and methods of using same. Moreover, it will be apparent that certain features of each embodiment can be used in combination with methods, systems, or apparatus illustrated or described in other embodiments. Accordingly, the above description should be construed as illustrative, and not in a limiting sense. All modifications, variations, or equivalent arrangements and implementations that are within the scope of the attached claims should therefore be considered within the scope of the invention.

Other combinations of the inventive features described above, of course easily can be determined by a skilled artisan after having read this specification, and are included in the spirit and scope of the claimed invention. References cited above are specifically incorporated in their entireties by reference and represent art known to the skilled artisan.

What is claimed is:

1. A catheter, comprising:
   an elongated tubular member having a proximal end, a distal end and a lumen extending between the proximal end and the distal end;
   a plurality of electrical cables bundled together and located within the lumen of the tubular member, a cross-section of the bundle of cables being substantially ovular or rectangular so as to be selectively bendable in two approximately opposite directions; and
   an ultrasound transducer adjacent the distal end of the tubular member,
   wherein a distal end of the plurality of electrical cables are coaxial cables and a distal end of the plurality of coaxial cables is connected to the ultrasound transducer, and
   wherein a section of the elongated tubular member adjacent the ultrasound transducer comprises:
      a hollow cylinder with a proximal end and a distal end and a first aperture and a second aperture, the first and second apertures opposing each other, wherein a steering cable is threaded through the proximal end of the hollow cylinder passing through a lumen of the hollow cylinder, out the first aperture, around an outer circumference of the hollow cylinder, and through the second aperture back into the lumen of the hollow cylinder and out the proximal end; and
      a flexible tubular member coaxially fitted over the proximal end of the hollow cylinder.

2. The catheter of claim 1, wherein the plurality of electrical cables are bundled together within a sheath.

3. The catheter of claim 1, wherein ends of the steering cable are connected forming an elongated loop, and
   wherein the catheter further comprises a steering device adjacent the proximal end of the elongated tubular member, the steering device being capable of manipulating the elongated loop thereby causing the distal end of the elongated tubular member to bend.

4. The catheter of claim 1, wherein
   the elongated tubular member includes a first section having a first Shore Durometer hardness, a second section distal the first section and having a second Shore Durometer hardness, the second Shore Durometer hardness being less than the first Shore Durometer hardness, and a third section distal the second section and having a third Shore Durometer hardness, the third Shore Durometer hardness being less than the second Shore Durometer hardness; and
   the ultrasound transducer is mounted on the elongate tubular member adjacent the third section,
      wherein the first section of the tubular member is capable of being bent at a first radius of curvature, the second section of the tubular member is capable of being bent at a second radius of curvature, the second radius of curvature being less than the first radius of curvature, and the third section of the tubular member is capable of being bent at a third radius of curvature, the third radius of curvature being less than the second radius of curvature.

5. The catheter of clam 4, wherein the first radius of curvature is no more than about four inches, the second radius of curvature is no more than about three inches, and the third radius of curvature is no more than about two inches.

6. The catheter of claim 4, wherein the first radius of curvature is no more than about three inches, the second radius of curvature is no more than about two inches, and the third radius of curvature is no more than about one inch.

7. The catheter of claim 4, wherein the first radius of curvature is no more than about two inches, the second radius of curvature is no more than about one inch, and the third radius of curvature is no more than about half an inch.

8. The catheter of claim 4, further comprising a plurality of coaxial cables bundled together and located within a lumen of the tubular member, the cross-section of the bundle of cables being substantially oval or rectangular so as to be preferentially bendable in two approximately opposite directions.

9. The catheter of claim 1,
   wherein the bundle of coaxial cables is twisted along its length so that a distal end of the bundle of cables is substantially perpendicular to a proximal end of the bundle of cables.

10. The catheter of claim 9, wherein the steering cable is a first steering cable being capable of bending the distal end of the elongated tubular member along a first plane that is substantially perpendicular to the distal end of the bundle of coaxial cables when a pulling force is applied to the first steering cable, and
    further comprising a second steering cable coupled to a region of the bundle of coaxial cables proximal to the distal end of the bundle of cables, the region being substantially perpendicular to the distal end of the bundle of coaxial cables, the second steering cable being capable of bending the distal end of the elongated tubular member along a second plane that is substantially parallel to the distal end of the bundle of coaxial cables when a pulling force is applied to the second steering cable.

11. The catheter of claim 10, wherein the first steering cable comprises a first end and a second end, and wherein a pulling force applied to the first end of the first steering cable causes the elongated tubular member to bend in a first direction, and a pulling force applied to the second end of the first steering cable causes the elongated tubular member to bend in a second direction opposite the first direction.

12. The catheter of claim 11, wherein the second steering cable comprises a first end and a second end, and wherein a pulling force applied to the first end of the second steering cable causes the elongated tubular member to bend in a third direction, and a pulling force applied to the second end of the second steering cable causes the elongated tubular member to bend in a fourth direction that is approximately opposite the third direction.

13. The catheter of claim 12, further comprising a steering device adjacent the proximal end of the elongated tubular member, the steering device being capable of manipulating the proximal ends of the first and second steering cables thereby causing the distal end of the elongated tubular member to bend in any of four directions.

14. The catheter of claim 1, wherein the catheter is disposable and adapted for single use.

15. The catheter of claim 1, wherein a first section of the elongated tubular member adjacent the ultrasound transducer is more flexible than a second section of the elongated tubular member proximal the first section.

16. The catheter of claim 15, wherein the first section of the elongated tubular member is capable of being bent at a first radius of curvature, and the second section of the elongated tubular member is capable of being bent at a second radius of curvature, wherein the second radius of curvature is greater than the first radius of curvature.

17. The catheter of clam 16, wherein the first radius of curvature is one of no more than about two inches; no more than about one inch, and no more than about half an inch.

18. The catheter of claim 16, wherein the second radius of curvature is one of no more than about three inches, no more than about two inches, no more than about one inch, and no more than about half an inch.

19. A catheter comprising:
an elongated tubular member having a proximal end, a distal end and a lumen extending between the proximal end and the distal end; and
a plurality of electrical cables bundled together and located within the lumen of the tubular member, a cross-section of the bundle of cables being substantially ovular or rectangular so as to be selectively bendable in two approximately opposite directions;
wherein a distal end of the plurality of electrical cables comprise coaxial cables and the distal end of the plurality of coaxial cables is connected to the ultrasound transducer,
wherein a section of the elongated tubular member adjacent the ultrasound transducer comprises:
a hollow cylinder with a proximal end and a distal end and a first aperture and a second aperture, the first and second apertures opposing each other, wherein a steering cable is threaded through the proximal end of the hollow cylinder passing through a lumen of the hollow cylinder, out the first aperture, around an outer circumference of the hollow cylinder, and through the second aperture back into the lumen of the hollow cylinder and out the proximal end; and
a flexible tubular member coaxially fitted over the proximal end of the hollow cylinder, and
wherein the catheter is an electrophysiology recording catheter further comprising an electrophysiology recording electrode within the catheter, wherein one of the plurality of electrical cables is connected to the electrophysiology recording electrode.

20. A catheter comprising:
an elongated tubular member having a proximal end, a distal end and a lumen extending between the proximal end and the distal end; and
a plurality of electrical cables bundled together and located within the lumen of the tubular member, a cross-section of the bundle of cables being substantially ovular or rectangular so as to be selectively bendable in two approximately opposite directions,
wherein a distal end of the plurality of electrical cables are coaxial cables and a distal end of the plurality of coaxial cables couples to an ultrasound transducer, and
wherein a section of the elongated tubular member adjacent the ultrasound transducer comprises:
a hollow cylinder with a proximal end and a distal end and a first aperture and a second aperture, the first and second apertures opposing each other, wherein a steering cable is threaded through the proximal end of the hollow cylinder passing through a lumen of the hollow cylinder, out the first aperture, around an outer circumference of the hollow cylinder, and through the second aperture back into the lumen of the hollow cylinder and out the proximal end; and
a flexible tubular member coaxially fitted over the proximal end of the hollow cylinder, and
wherein the catheter is an ablation catheter further comprising an ablation electrode operatively coupled to the ablation catheter, wherein one of the plurality of electrical cables is connected to the ablation electrode.

21. A steerable ultrasound catheter comprising:
a transducer array;
a plurality of coaxial cables forming a bundle, the bundle having a proximal end and a distal end, the distal end of the bundle being connected to the transducer array, a cross-section of the bundle being substantially ovular or rectangular so as to be bendable in two approximately opposite directions;
a first cylinder having a first aperture, a second aperture opposing the first aperture, a proximal end with an opening, a distal end with an opening, and a lumen extending between the proximal end and the distal end of the first cylinder, the bundle of coaxial cables being inserted through the opening in the distal end of the first cylinder;
a steering cable threaded through the opening in the proximal end of the first cylinder passing through the lumen of the first cylinder, out the first aperture, around an outer circumference of the first cylinder, and through the second aperture back into the lumen of the first cylinder and back out the opening in the proximal end of the first cylinder;
a second cylinder having a proximal end with an opening, a distal end with an opening, and a lumen extending between the proximal end and the distal end of the second cylinder, wherein the first cylinder is inserted through the opening in the distal end of the second cylinder and the steering cable extends through the lumen of the second cylinder and out the opening at the proximal end of the second cylinder; and
an elongated tubular member that is fitted over the proximal end of the second cylinder and receives the bundle of coaxial cables and the steering cable.

22. The catheter of claim 21, where the lumen of the first cylinder comprises an ovular or rectangular cross-section shaped to receive the bundle of coaxial cables.

23. The catheter of claim 21, wherein the plurality of coaxial cables is bundled together within a sheath.

24. The catheter of claim 21, wherein the proximal end of the bundle of coaxial cables is adapted for connection to an ultrasound machine.

25. The steerable ultrasound catheter of claim 21, wherein
the elongated tubular member includes a proximal end, a distal end, and lumen extending between the proximal end and the distal end of the elongated tubular member; and
the steering cable includes a first section, a second section, and a third section, the steering cable being threaded through the elongated tubular member such that the first and third sections are adjacent one another and are separated from one another at the second section which forms a loop around the distal end of the elongate tubular member.

26. The steerable ultrasound catheter of claim 25 further comprising a steering element attached to the first and third sections of the steering cable, the steering element being capable of applying a pulling force on the first and third sections independently of one another.

27. The steerable ultrasound catheter of claim 26, wherein a first pulling force applied to the first section bends the catheter in a first direction, and a second pulling force applied to the third section bends the catheter in a second direction approximately opposite the first direction.

28. The steerable ultrasound catheter of claim 25, wherein the first and third sections are intertwined.

29. The steerable ultrasound catheter of claim 25, wherein the first and third sections of the steering cable are located within the lumen of the first cylinder.

30. The steerable ultrasound catheter of claim 25, wherein the steering cable comprises a polymer material.

31. A method of imaging an anatomical structure of a mammal comprising:
providing an ultrasound catheter comprising:
an elongated tubular member having a proximal end, a distal end and a lumen extending between the proximal end and the distal end of the elongated tubular member;
a plurality of coaxial cables bundled together and located within the lumen of the elongated tubular member, a cross-section of the bundle of cables being substantially ovular or rectangular so as to be bendable in two approximately opposite directions; and
an ultrasound transducer adjacent the distal end of the tubular member, wherein the plurality of electrical cables comprise coaxial cables and a distal end of the plurality of coaxial cables is connected to the ultrasound transducer, and wherein a section of the elongated tubular member adjacent the ultrasound transducer comprises:
a hollow cylinder with a proximal end and a distal end and a first aperture and a second aperture, the first and second apertures opposing each other, wherein a steering cable is threaded through the proximal end of the hollow cylinder passing through a lumen of the hollow cylinder, out the first aperture, around an outer circumference of the hollow cylinder, and through the second aperture back into the lumen of the hollow cylinder and out the proximal end; and
a flexible tubular member coaxially fitted over the proximal end of the hollow cylinder;
making an incision in the mammal;
inserting the ultrasound catheter through the incision;
advancing the ultrasound catheter into the anatomical structure by bending the distal end of the elongated tubular member along the longer sides of the ovular or rectangular cross-section of the bundle of cables while pushing the ultrasound catheter forward relative to the incision; and
activating the ultrasound transducer to take a first image of the anatomical structure.

32. The method of claim 31, further comprising bending the distal end of the elongated tubular member along the longer sides of the ovular or rectangular cross-section of the bundle of cables and taking a second image from an angle different from an angle from which the first image was taken.

33. The method of claim 31, further comprising rotating the distal end of the elongated tubular member prior to bending the distal end of the elongated tubular member.

34. A method of steering a catheter within a body, comprising:
advancing the catheter within the body, the catheter comprising:
an elongated tubular member having a proximal end, a distal end and a lumen extending between the proximal end and the distal end of the elongated tubular member;
a plurality of electrical cables bundled together and located within the lumen of the tubular member, a cross-section of the bundle of electrical cables being substantially ovular or rectangular so as to be selectively bendable in two approximately opposite; and
an ultrasound transducer,
wherein a section of the elongated tubular member adjacent the ultrasound transducer comprises:
a hollow cylinder with a proximal end and a distal end and a first aperture and a second aperture, the first and second apertures opposing each other, wherein a steering cable is threaded through the proximal end of the hollow cylinder passing through a lumen of the hollow cylinder, out the first aperture, around an outer circumference of the hollow cylinder, and through the second aperture back into the lumen of the hollow cylinder and out the proximal end; and
a flexible tubular member coaxially fitted over the proximal end of the hollow cylinder;
applying a first force to the bundle of electrical cables to cause the distal end of the elongated tubular member to form a bend; advancing the catheter within the body; and
applying a second force to the bundle of electrical cables to remove the bend in the distal end of the elongated tubular member, wherein the second force is substantially opposite the first force.

35. The method of claim 34, wherein the catheter further comprises at least one steering cable coupled to the distal end of the elongated tubular member and extending proximally to the proximal end of the elongated tubular member, the at least one steering cable being capable of bending the distal end of the elongated tubular member when a pulling force is applied to the at least one steering cable, and wherein the first force is applied by applying a pulling force on a first end of the at least one steering cable, and the second force is applied by applying a pulling force on a second end of the at least one steering cable.

* * * * *

UNITED STATES PATENT AND TRADEMARK OFFICE
CERTIFICATE OF CORRECTION

PATENT NO. : 7,507,205 B2
APPLICATION NO. : 10/819358
DATED : March 24, 2009
INVENTOR(S) : Simcha Borovsky et al.

It is certified that error appears in the above-identified patent and that said Letters Patent is hereby corrected as shown below:

Column 26, claim 34, line 29 after "opposite" and before the ";", kindly insert --directions--.

Signed and Sealed this
Nineteenth Day of February, 2013

Teresa Stanek Rea
*Acting Director of the United States Patent and Trademark Office*